United States Patent [19]

Wolf

[11] 4,059,434

[45] Nov. 22, 1977

[54] CYCLOALKANAPYRAZOLE HERBICIDES

[75] Inventor: Anthony David Wolf, Newark, Del.

[73] Assignee: E. I. Du Pont de Nemours and Company, Wilmington, Del.

[21] Appl. No.: 717,014

[22] Filed: Aug. 26, 1976

Related U.S. Application Data

[63] Continuation-in-part of Ser. No. 622,763, Oct. 15, 1975, abandoned, and Ser. No. 640,348, Dec. 12, 1975, abandoned.

[51] Int. Cl.$^2$ ...................... A01N 9/22; C07D 231/56

[52] U.S. Cl. ........................................ 71/92; 71/76; 548/372

[58] Field of Search ........................ 260/310 R; 71/92

[56] References Cited

U.S. PATENT DOCUMENTS 3,364,227 1/1968 Robinson et al. ........................ 71/92

OTHER PUBLICATIONS

Nunn et al. Chemical Abst. vol. 82, 170804a 1975.

Nunn et al. Chem. Abst. vol. 84, 90084s 1976.

*Primary Examiner*—James O. Thomas, Jr.

*Assistant Examiner*—Jane T. Fan

[57] ABSTRACT

Herbicidal cycloalkanapyrazoles of the formula:

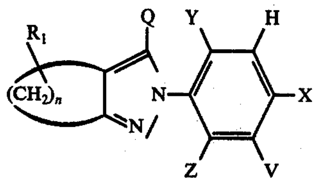

(I)

where n is 3, 4 or 5;

$R_1$ is hydrogen or methyl;

Q is fluorine, chlorine, bromine or iodine;

X is fluorine, chlorine, bromine, iodine, cyano, methoxy or nitro;

Y is hydrogen, fluorine, or chlorine;

Z is hydrogen or fluorine; and

V is hydrogen, fluorine, chlorine or methoxy with the proviso that a. when n is 5, $R_1$ must be hydrogen, Q must be chlorine or bromine, Z and V must both be hydrogen and Y must be hydrogen or fluorine;

b. when n is 3 or 4 and Q is fluorine or iodine, $R_1$, Z and V must be hydrogen and Y must be hydrogen or fluorine;

c. when n is 3 and $R_1$ is methyl, Q must be chlorine or bromine, Y must be hydrogen or fluorine and Z and V must both be hydrogen; and, d. when V is other than hydrogen, X must be fluorine, chlorine or bromine and Z must be hydrogen.

105 Claims, No Drawings

CYCLOALKANAPYRAZOLE HERBICIDES

CROSS REFERENCE TO RELATED APPLICATIONS

This application is a continuation-in-part of my copending applications Ser. No. 622,763, filed Oct. 15, 1975, now abandoned and Serial No. 640,348, filed Dec. 12, 1975, now abandoned.

BACKGROUND OF THE INVENTION

Recently, in German Offenlegungsschrift No. 2,165,651 a group of isoindole-1,3-diones which are useful as herbicides was disclosed. The general formula for the isoindole-1,3-diones disclosed in the Offenlegungsschrift is as follows:

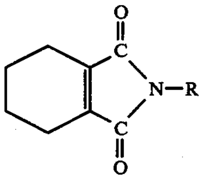

wherein R may be an aryl, aralkyl or benzyl substituent optionally substituted with 1 to 5 halogen atoms or a hydroxy, nitro, cyano, thiocyanato, carboxy, alkyl or halogenated alkyl, alkoxy, lower alkylthio or phenyl group. R may also be optionally substituted with a group having the configuration —O—$CH_2$A where A is phenyl or a naphthyl group. The phenyl group may contain one or more halogen atoms, nitro groups, lower alkyl groups or lower alkoxy groups.

Typical of the compounds disclosed in the Offenlegungsschrift is the compound of Structure 1:

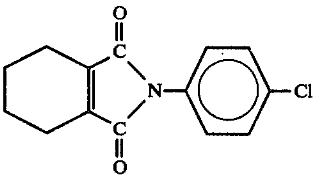

(1)

Although the compounds disclosed within the Offenlegungsschrift are active herbicides, the need still exists for even better herbicides. Weeds are very damaging to important crops such as rice and wheat and they decrease crop yield. In the current world situation, wherein food shortages are acute, it is most important to harvest the maximum possible yields of crops such as rice or wheat. Thus, a need exists for a particularly effective herbicide which will destroy as many weeds as possible without causing significant damage to desired crops, e.g., rice or wheat.

According to the instant invention, compounds have been discovered which are highly active herbicides and yet cause minimal damage to certain desired crops, e.g., rice and wheat, and especially the major world food crop, rice.

The preparation and fungicidal utility of the 2-(4-chlorophenyl)-1,2,4,5,6,7-hexahydroindazol-3(3H)-one is disclosed in Takeda Chem. Ind. Paper, Chem. Abs., 67, 11542h (1967).

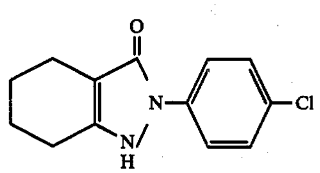

2-Aryl-4,5,6,7-tetrahydro-1-alkyl-1H-indazol-3(2H)-ones are claimed as antipyretics in Ger. 668.628 [assigned to P. Bierdorf & Co. AG, Chem. Abs., 33, 5131[2](1939)] and U.S. Pat. No. 2,104,348 [assigned to E. R. Squibb, Co., Chem. Abs., 32, 1869[1] (1938)].

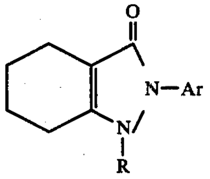

German Offenlegungsschrift No. 2,409,753 discloses herbicides having the general formula

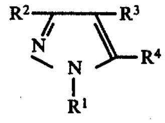

in which $R^1$ is hydrogen, an alkyl, cycloalkyl or aralkyl radical, a phenyl group which may be substituted or an acyl radical having the formula —CO—$R^6$ or

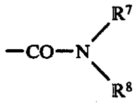

$R^6$ is hydrogen, an alkyl radical which may be substituted, an alkoxy or phenoxy radical or a phenyl radical and $R^7$ and $R^8$ are the same or different and can be hydrogen, alkyl, phenyl which may be substituted or alkinyl, $R^2$ is an alkyl radical which may be substituted, a cycloalkyl radical or a phenyl radical which may be substituted or a heterocyclic radical with O, N or S atoms in the ring, $R^3$ is hydrogen, chlorine, bromine or a low-molecular-weight alkyl radical, $R^4$ is the radical —S—$R^5$, —SO—$R^5$ or —$SO_2$—$R^5$ and $R^5$ is an alkyl radical, cycloalkyl radical, aralkyl radical or a phenyl group which may be substituted or a heterocyclic radical with O, N or S in the ring.

An intermediate for preparing these herbicides by reaction with a mercaptan having the general formula $R_5$SH is

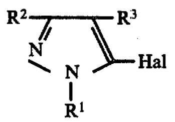

where $R^1$, $R^2$, $R^3$ and $R^5$ have the previously given meanings and Hal represents chlorine, bromine or iodine.

1-Phenyl-3,4-trimethylenepyrazolone is disclosed in U.S. Pat. No. 1,685,407 (1928) with utility as an intermediate for making dyes and medicinal compounds. C. Mannich in Arch. Pharm. 267, 699–702 (1929) and in Brit. 260,577 describes the preparation of 1-phenyl-3,4-trimethylenepyrazolones.

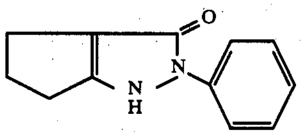

R. P. Willliams et al. in J. Med. Chem. 13, 773 (1970) reports the preparation and evaluation as anti-inflammatory agents compounds of the following type:

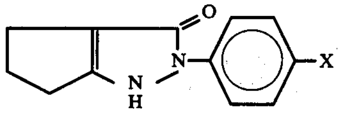

X = H, Br, F.

DESCRIPTION OF THE INVENTION

This invention relates to the novel compounds of Formula I and to agricultural compositions containing them, and to the method of use of these compounds as selective, as well as general, herbicides having both pre- and post-emergence activity.

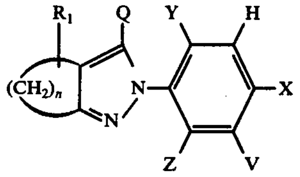

(I)

where n is 3, 4 or 5;

$R_1$ is hydrogen or methyl;

Q is fluorine, chlorine, bromine or iodine;

X is fluorine, chlorine, bromine, iodine, cyano, methoxy or nitro;

Y is hydrogen, fluorine, or chlorine;

Z is hydrogen or fluorine; and

V is hydrogen, fluorine, chlorine or methoxy with the proviso that a. when n is 5, $R_1$ must be hydrogen, Q must be chlorine or bromine, Z and V must both be hydrogen and Y must be hydrogen or fluorine;

b. when n is 3 or 4 and Q is fluorine or iodine, $R_1$, Z and V must be hydrogen and Y must be hydrogen or fluorine;

c. when n is 3 and $R_1$ is methyl, Q must be chlorine or bromine, Y must be hydrogen or fluorine and Z and V must both be hydrogen; and d. when V is other than hydrogen, X must be fluorine, chlorine or bromine and Z must be hydrogen.

Of those compounds of Formula I, preferred for their high herbicidal activity or favorable cost or both, are those compounds where, independently, 1. n is 3 or 4;
2. Q is chlorine or bromine;
3. $R_1$ is hydrogen or methyl;
4. Z and V are both hydrogen;
5. Y is hydrogen or fluorine; or,
6. X is fluorine, chlorine, bromine, cyano or methoxy.

Of those compounds of Formula I where n is 4, preferred are those where Q is chlorine or bromine.

More preferred are those compounds where n is 4, Q is chlorine or bromine, and $R_1$ is hydrogen.

Of those compounds of Formula I where n is 4, Q is chlorine or bromine and $R_1$ is hydrogen, preferred are those compounds where, independently, 1. Z and V are both hydrogen;
2. Y is hydrogen or fluorine; or
3. X is fluorine, chlorine, bromine, cyano or methoxy.

More preferred still are those compounds where n is 4, Q is chlorine or bromine, $R_1$ is hydrogen and Z and V are both hydrogen.

Of those compounds of Formula I where n is 4, Q is chlorine or bromine, $R_1$ is hydrogen and Z and V are both hydrogen, preferred for their higher herbicidal activity or more favorable cost or both, are those compounds where, independently, 1. Y is hydrogen or fluorine; or,
2. X is fluorine, chlorine, bromine, cyano or methoxy.

More preferred are those compounds where n is 4, Q is chlorine or bromine, $R_1$ is hydrogen, Z and V are both hydrogen, Y is hydrogen or fluorine and X is fluorine, chlorine, bromine, cyano or methoxy.

Most preferred for their excellent herbicidal activity or highly favorable cost or both are those compounds of Formula I where n is 4, Q is chlorine or bromine, $R_1$ is hydrogen, Z and V are both hydrogen, Y is hydrogen or fluorine, and X is chlorine or bromine.

Of those compounds of Formula I where n is 3, preferred are those compounds where Q is chlorine or bromine.

More preferred are those compounds where n is 3, Q is chlorine or bromine, and $R_1$ is hydrogen.

Of those compounds of Formula I where n is 3, Q is chlorine or bromine and $R_1$ is hydrogen, preferred are those compounds where, independently, 1. Z and V are both hydrogen;
2 Y is hydrogen or fluorine; or,
3. X is fluorine, chlorine, bromine, cyano or methoxy.

Most preferred are those compounds where n is 3, Q is chlorine or bromine, $R_1$ is hydrogen and Z and V are both hydrogen.

Of those compounds of Formula I where n is 3, Q is chlorine or bromine, $R_1$ is hydrogen and Z and V are both hydrogen, preferred for their higher herbicidal activity or more favorable cost or both, are those compounds where, independently, 1. Y is hydrogen or fluorine; or,
2. X is fluorine, chlorine, bromine, cyano or methoxy.

More preferred are those compounds where n is 3, Q is chlorine or bromine, $R_1$ is hydrogen, Z and V are both hydrogen, Y is hydrogen or fluorine and X is fluorine, chlorine, bromine, cyano or methoxy.

Most preferred for their excellent herbicidal activity or highly favorable cost or both are those compounds of Formula I where n is 3, Q is chlorine or bromine, $R_1$ is hydrogen, Z and V are both hydrogen, Y is hydrogen or fluorine, and X is chlorine or bromine.

Of those compounds of Formula I, preferred for their high herbicidal activity or favorable cost or both, are those compounds where Y is hydrogen or fluorine and Z and V are both hydrogen.

More preferred are those compounds where Y is hydrogen or fluorine and Z and V are both hydrogen where, independently, 1. Q is chlorine; or,
2. X is chlorine or bromine.

Of those compounds of Formula I, preferred for their higher herbicidal activity or more favorable cost or both, are those compounds where Y is hydrogen or fluorine, Z and V are both hydrogen and Q is chlorine.

Most preferred for their excellent herbicidal activity or highly favorable cost or both are those compounds of Formula I where Y is hydrogen or fluorine, Z and V are both hydrogen, Q is chlorine, and X is chlorine or bromine.

Specifically preferred for thier outstanding herbicidal activity or favorable cost or both are 1. 3-Chloro-2-(4-chloro-2-fluorophenyl)-4,5,6,7-tetrahydro-2H-indazole; m.p. 88°-89.5° C;
2. 3-Chloro-2-(4-chlorophenyl)-4,5,6,7-tetrahydro-2H-indazole; m.p. 81°-84°;
3. 3-Bromo-2-(4-chloro-2-fluorophenyl)-4,5,6,7-tetrahydro-2H-indazole; m.p. 95°-98° C;
4. 3-Chloro-2-(4-bromo-2-fluorophenyl)-4,5,6,7-tetrahydro-2H-indazole; m.p. 86°-88° C;
5. 3-Chloro-2-(4-chloro-2-fluorophenyl)-2,4,5,6-tetrahydrocyclopentapyrazole; m.p. 101.5°-104° C; and ,
6. 3-Chloro-2-(4-chlorophenyl)-2,4,5,6-tetrahydrocyclopentopyrazole; m.p. 114.5°-117° C.

SYNTHESIS OF THE COMPOUNDS

The novel cycloalkanapyrazoles of Formula I where Q is Cl or Br are prepared in two steps as shown by Equations A and B:

A.

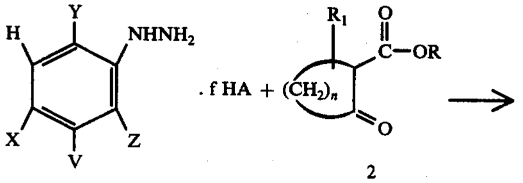

1 2

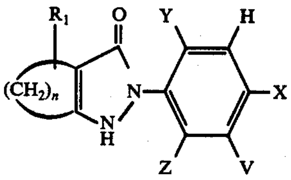

3

B.

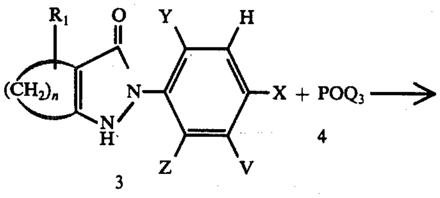

3

-continued

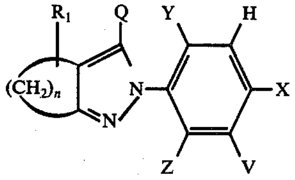

I where $R_1$, n, X, Y, V and Z are as defined above;

Q is Br or Cl;

R is alkyl of 1 to 3 carbon atoms;

f is 0 or 1; and

A is an anion of the corresponding acid HA having an ionization constant of at least $1 \times 10^{-7}$, e.g. $H_2SO_4$ or HCl.

The preparation of the annelated pyrazolones 3 is known in the literature; for example, the preparation of 2-aryl-1,2,4,5,6,7-hexahydro-3H-indazol-3-ones (3, n = 4) is described in W. Dieckmann, Ann., 317, 102 (1901). The β-keto ester 2 is combined with the appropriate aryl hydrazine acid salt 1 in an appropriate solvent, such as a lower alcohol, or aromatic hydrocarbon, and, optionally, in the presence of an acid acceptor, such as a tertiary organic amine or alkali metal hydroxide or alkoxide and the reaction mixture is heated at reflux for 0.5-24 hours. The pyrazolone 3 is isolated by conventional techniques such as by pouring the reaction mass into water and filtering the product. The crude product is usually of sufficient purity to be used directly in the next step. If necessary, further purification can be accomplished by recrystallization, sublimation, or other conventional techniques known to those skilled in the art. This same procedure can be used to prepare those compounds of formula 3 in which n = 5.

The pyrazolones 3 where n is 3 are prepared by combining the appropriate aryl hydrazine with the appropriate alkyl 2-oxocyclopentanecarboxylate in a suitable solvent such as toluene or chlorobenzene. The reaction is heated at reflux and water is simultaneously removed to yield a hydrazone. Cyclization to the pyrazolones 3 where n is 3 is then effected by adding 1-3 equivalents of an alkali metal alkoxide such as sodium methoxide to the hydrazone solution and heating for 1-5 hours at 80°-130° C.

Methods taught in Arch. Pharm., 267, 699-702 (1929) and in J. Med. Chem., 13, 733 (1970) are also useful in preparing pyrazolones of fromula 3 in which n = 3.

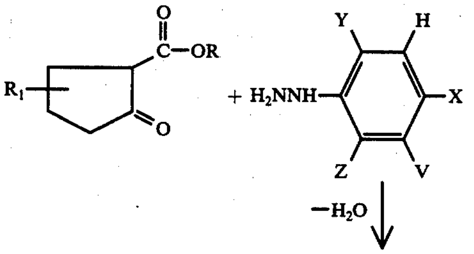

-continued

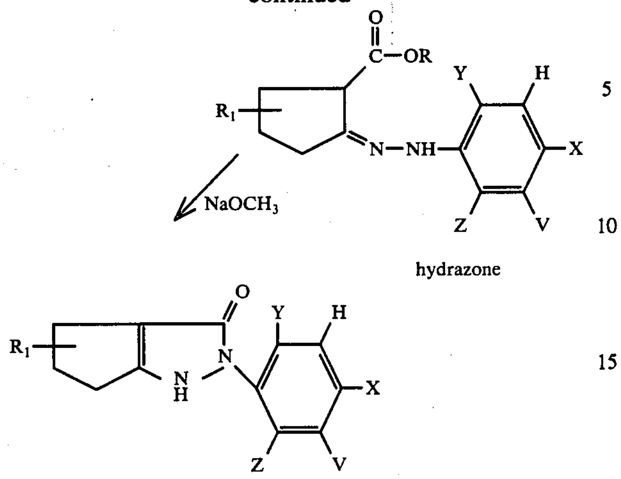

Alternatively, the hydrazone may be isolated and subsequently cyclized by treatment with the two equivalents of n-butyl lithium in a solvent such as THF at temperatures of 0°-60° C for a period of 2-18 hours.

The pyrazolones 3 where n is 3 are isolated by pouring the reaction mass into water, separating the organic layer and acidifying the aqueous layer with a mineral acid, i.e., HCl, $H_2SO_4$. From the acidified aqueous layer the desired product is obtained by filtration, centrifugation, extraction or other similar techniques.

The novel cycloalkanapyrazoles of Formula I hich Q is chlorine are obtained by heating the annelated pyrazolones 3 with phosphorous oxychloride (formula 4, Q is chlorine). When Q is bromine in Formula 1, phosphorous oxybromide (formula 4, Q is bromine) in the presence of an N,N-dialkylaniline and dimethylformamide is used (Equation B).

The use of an inert organic solvent such as methylene chloride or toluene is optional; however, it is preferred that no solvent other than the phosphorous oxychloride or bromide be used. The mixture is heated at 100°-180° C, preferably 140°-150° C., for a period of 1-10 hours. The crude reaction mixture is dissolved in an inert organic solvent (e.g., $CHCl_3$, $CH_2Cl_2$, or toluene), and the solution is washed with dilute aqueous base (e.g., NaOH or KOH) followed with water. The organic phase is dried, and the solvent is removed on a rotary evaporator or by distillation. The product obtained is the pyrazole of Formula I and may be purified by distillation, sublimation or crystallization from an appropriate solvent.

Compounds of Formula I where Q is iodine are prepared from corresponding aminopyrazoles via diazotization with nitrous acid and reaction with potassium iodide according to the method of Spanish Pat. No. 394,208 [Chem Abst., 83, 972834 (1975)]. The required aminopyrazoles are prepared from the appropriate α-cyanocyclohexanone or α-cyanocyclopentanone by reaction with appropriate aryl hydrazine in a solvent such as toluene. The overall sequence for preparing compounds of Formula I where Q is iodine is illustrated by equation $A_2$ and $B_2$:

$A_2$ & $B_2$:

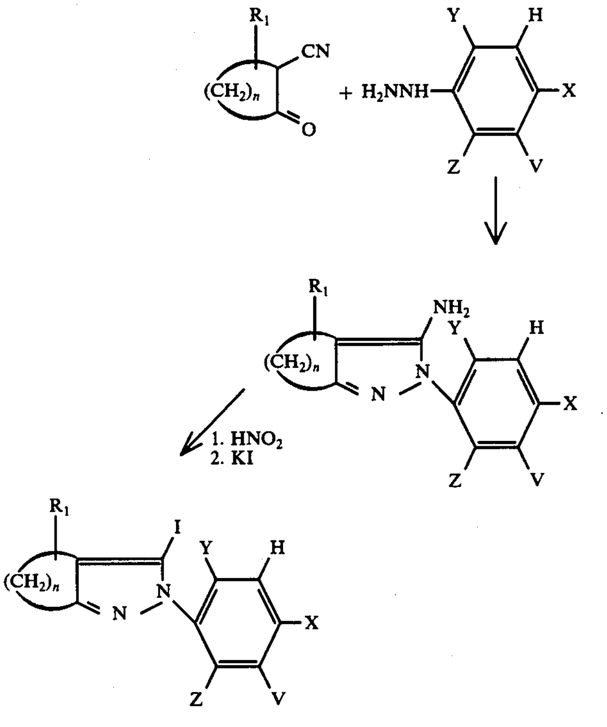

I

The required α-cyanoketones can be prepared by a number of methods as well known in the art. For examples, α-cyanocyclohexanone is prepared from α-chlorohexanone and sodium cyanide according to R. Meyer in Helv. Chim. Acta, 16, 1291 (1933). α-Cyanocyclopentanone is prepared from adiponitrile and a strong base such as a lithium dialkylamide followed by acid hydrolysis according to Ger. 591,269 (Jan., 1934) [C.A. 28, 117 (1934)]. α-Cyanocycloaliphatic ketones can also be prepared from cycloalkanone enamines and cyanogen chloride according to the method of M. E. Kuehne, J. Am. Chem. Soc., 81, 5400 (1959).

Compounds of Formula I where Q is fluorine are prepared as shown in equations $A_3$and $B_3$ from photolysis of corresponding 3-diazonium fluoborate (equation $B_3$) which in turn are obtained by diazotization of 3-aminopyrazoles with nitrous acid in fluoboric acid (equation $A_3$) according to the method of E. D. Bergmann, J. Am. Chem. Soc., 78, 6037 (1956).

$A_3$ and $B_3$

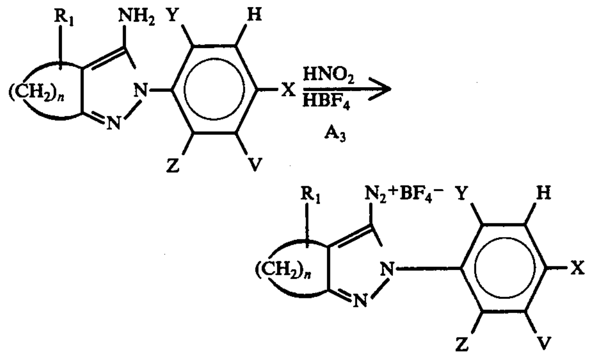

-continued

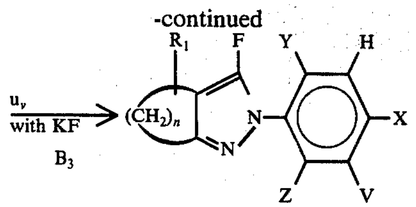

Intermediate $\beta$-keto esters 2 are commercially available or are prepared by methods well described in the literature: G. Stork et al., J. Am. Chem. Soc., 85, 207 (1963). The general procedure is shown in Equations C, D and E:

C.

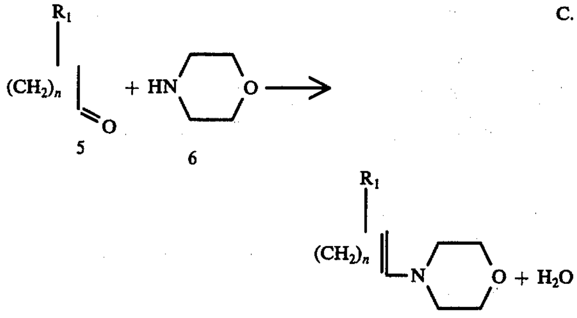

5 6

7

D.

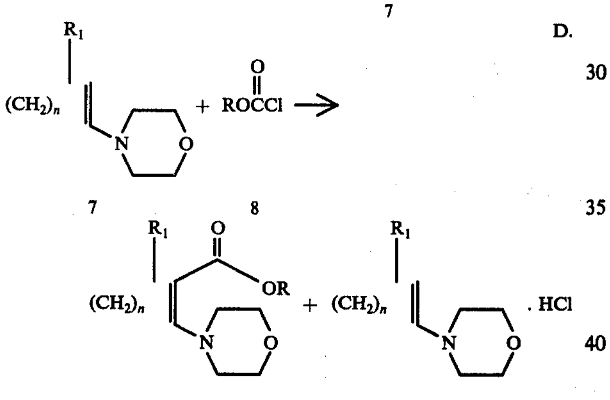

7 8

9 10

E.

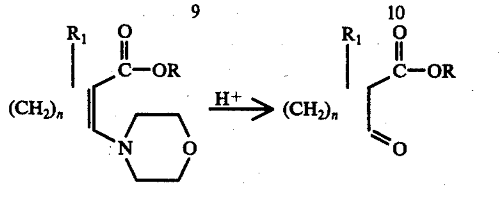

9 2

Enamine 7 is prepared by heating ketone 5 and morpholine 6 (pyrrolidine may also be used) in an appropriate solvent, such as benzene, toluene, or chlorobenzene, with simultaneous removal of water from the reaction by azeotropic distillation (Equation C). The alkyl chloroformate 8 is added to the enamine 7, and this mixture is heated at a temperature from 70° C to the boiling point of the solvent for a period of 1-10 hours. The enamine hydrochloride 10 which is produced as a by-product in the reaction is removed by filtration. The morpholine enamine 9, which is contained in the organic filtrate, is converted to the $\beta$-keto ester 2 hydrolysis with aqueous mineral acid (e.g., hydrochloric acid) at temperatures ranging from ambient to 75° C (Equation E). The product is isolated by conventional techniques such as extraction into a suitable organic solvent followed by evaporation of the solvent. The product may be further purified by fractional distillation under reduced pressure, sublimation, or crystallization.

The use of 3-methylcyclohexanone 5a leads to a mixture of methyl-substituted $\beta$-keto esters (2a and 2b). If this mixture of methyl-substituted $\beta$-keto esters is reacted with an aryl hydrazine, a mixture of 4- and 6-methyl-substituted-2-aryl-1,2,4,5,6,7-hexahydro-3H-indazol-3-ones (3a and 3b) is produced; subsequent treatment with phosphorous oxyhalide 4 will produce a mixture containing both the 4- and 6-methyl-substituted-3-halo-2-aryl-tetrahydroindazoles of this invention. If the mixture of isomeric methyl cyclohexanones is separated, then 2a and 2b will lead to 3a an 3b respectively when treated with an arylhydrazine.

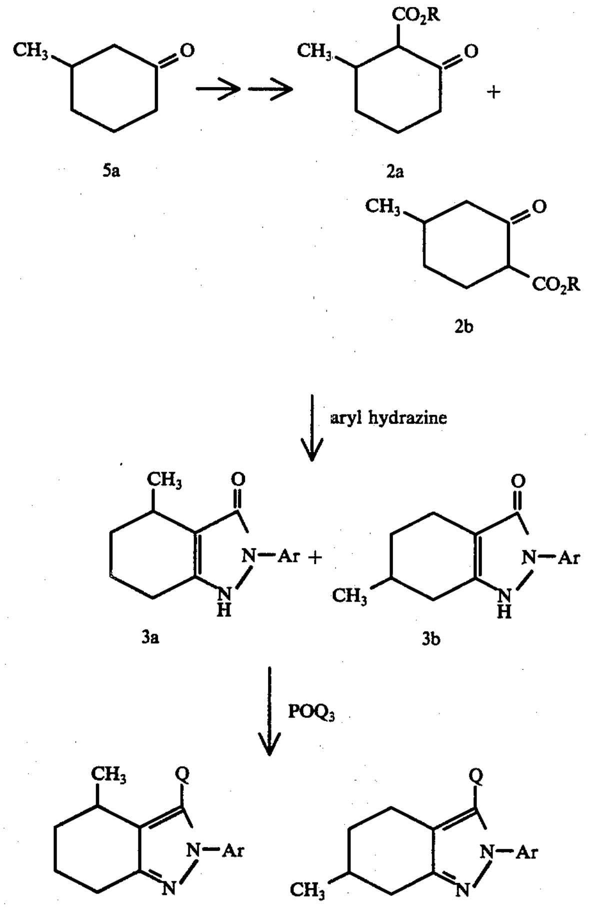

5a 2a 2b 3a 3b

In the case of the 2- or 4-methylcyclohexanones, the $\beta$-keto ester synthesis is more specific and predominately one isomer is produced, as summarized schematically in Equations F and G. 2-Methylcyclohexanone produces 7-methyl-3-halo-2-aryl-4,5,6,7-tetrahydroindazole, and 4-methylcyclohexanone produces 5-methyl-3-halo-4,5,6,7-tetrahydroindazoles.

F.

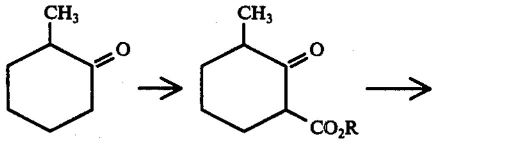

-continued

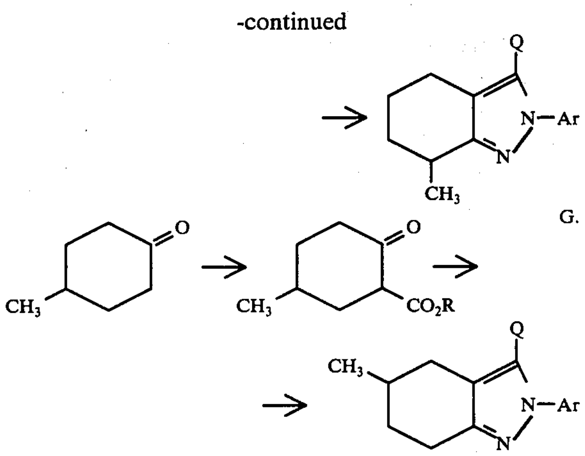

G.

The required alkyl-2-oxocyclopentanecarboxylates can be prepared by methods previously described and by methods described in *Organic Reactions,* 15, 1-203 (1967).

The preparation of aryl hydrazines 1 from anilines is well documentated in the literature: G. H. Coleman, *Organic Syntheses, Coll. Vol. I,* J. Wiley & Sons, New York, p. 442 and H. Kindler et al., Fr. 1,419,092. A general procedure is illustrated in Equation H:

H.

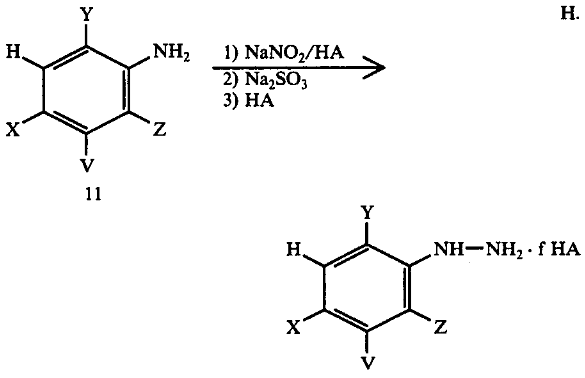

11

1

The aniline 11 is diazotized at about −5 to 5° C with sodium nitrite in aqueous acid (HA, where A is defined as above) such as hydrochloric acid; the resulting solution is mixed with an aqueous sodium bisulfite solution at 0°-20° C, heated to 50°-80° C for 0.5-2 hr. and then acidified with the mineral acid to give the aryl hydrazine acid salt 1. The hydrazine salt often crystallizes directly from the reaction mixture and can be isolated by filtration or by other conventional techniques. In most instances the hydrazine can be used without further purification.

Certain hydrazines used in preparing compounds defined by this invention are novel; e.g., 4-chloro-2-fluorophenylhydrazine hydrochloride is a novel compound which can be prepared by the method described above. The following novel hydrazines can also be prepared by this method:

4-bromo-2-fluorophenylhydrazine hydrochloride
2-fluoro-4-methoxyphenylhydrazine hydrochloride
2,4,6-trifluorophenylhydrazine hydrochloride
2-fluoro-4-nitrophenylhydrazine hydrochloride
4-cyano-2-fluorophenylhydrazine hydrochloride Also useful for preparing aryl hydrazines is the method described by M. S. Gibson et al., *J. Chem. Soc.* (C) 1970, 2106 and M. S. Gibson et al., *J. Chem. Soc.* (C), 1974, 215.

Representative aniline starting materials for these hydrazines are prepared as described below. 4-Chloro-2-fluoroaniline, for example, can be prepared from 2'-fluoroacetanilide [G. Schiemann and H. G. Baumaarten, Chem. Berichte, 70, 1416 (1937)] by the reaction sequences shown below:

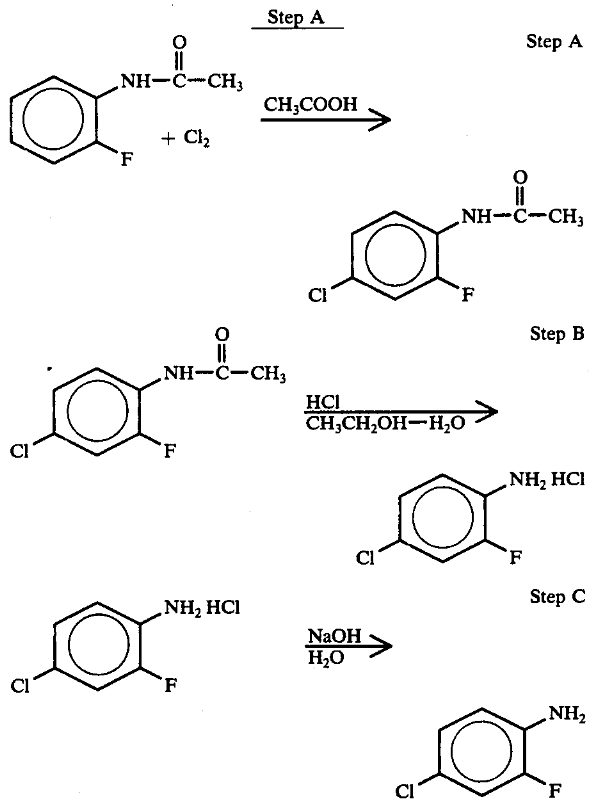

STEP A

Chlorination of acetanilides in acetic acid is well known to those skilled in the art and may be carried out under the condition taught in W. W. Reed and K. J. P. Orton, *J. Chem. Soc.,* 91, 1543 (1907) for the chlorination of acetanilide. The chlorination of 2'-fluoroacetanilide takes place at 25°-30° C over several hours (e.g. 5) at atmospheric pressure. The resulting product is 4'-chloro-2'-fluoroacetanilide.

STEP B

The chlorofluoroacetanilide is refluxed in a mixture of a lower alcohol (50%) (e.g. ethanol) and concentrated hydrochloric acid (50%) for several hours (e.g. 5 or more) at 70°-90° C and atmospheric pressure. The solvent mixture is removed at a reduced pressure of 100 to 300 mm. Hg and at a temperature of 20°-50° C. to leave a residue of the hydrochloride salt of 4-chloro-2-fluoroaniline.

STEP C

After basification of an aqueous solution of the hydrochloride salt of 4-chloro-2-fluoroaniline with an alkali metal hydroxide solution, such as 50% sodium hydroxide at ambient conditions, the free 4-chloro-2-fluoroaniline is extracted into a suitable water-immiscible organic solvent such as ethyl ether or methylene chloride. Crude 4-chloro-2-fluoroaniline is isolated by removal of the organic solvent under a reduced pressure of 100 to 300 mm. Hg at 20°-50° C.

2-Fluoro-4-bromoaniline can be prepared by bromination of 2-fluoroaniline [prepared in Chem. Berichte, 70, 1416 (1937)] with N-bromosuccinimide as shown in the following equation.

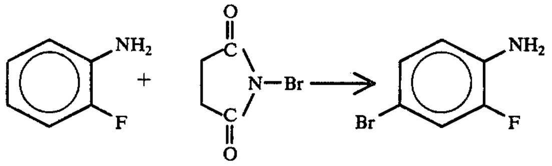

Bromination of anilines using N-bromosuccinimide in an inert organic solvent such as methylene chloride is well known to those skilled in the art, e.g., J. B. Wommack et al., J. Het. Chem., 6, 243 (1969). Bromination of 2-fluoroaniline is a exothermic reaction that takes place at 0° C over several hours, e.g. 5 or more. The resulting reaction mixture is washed with water several times and dried with an appropriate drying agent such as anhydrous sodium sulfate. The 4-bromo-2-fluoroaniline is recovered by removal of the organic solvent under a reduced pressure of 100 to 300 mm. Hg at 20°-50° C.

2,4,6-Trifluoroaniline is prepared by reduction of 1,3,5-trifluoro-2-nitrobenzene [V. I. Siele and H. J. Matsugama, U.S. Department Commerce, Office Serv., P B Rept. 145, 510, p. 1 (1960) or Chem. Abst., 56, 15394c (1962)] using the procedures described by G. Schiemann and M. Seyhan, Chem. Berichte, 70, 2396 (1937).

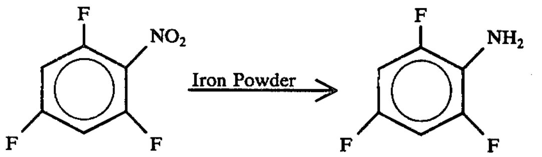

2,4-Difluoroaniline is known to the art and can be prepared by the procedure described in G. Scheimann and M. Seyhan Chem. Berichte, 70, 2396 (1937).

4-Amino-3-fluorobenzonitrile, used in the preparation of 4-cyano-2-fluorophenylhydrazine hydrochloride, can be prepared from 4-bromo-2-fluoroaniline by treatment with cuprous cyanide in N-methylpyrrolidone using known procedures: L. Friedman, et al., J. *J. Chem.*, 26, 2522 (1961). The reaction mixture is heated to reflux for several hours and then poured onto ice and sodium cyanide. The resulting solution is heated between 50°-80° C for a period of 1-3 hours, cooled, and extracted with toluene; the toluene extract is washed with water, dried with suitable drying agent, and evaporated to give 4-amino-3-fluorobenzonitrile.

2-Fluoro-4-methoxyaniline, used in the preparation of 2-fluoro-4-methoxyphenylhydrazine hydrochloride, is known and can be prepared by the method of H. Hodgson, et al., *J. Chem. Soc.*, 1268 (1940).

2-Fluoro-4-nitroaniline, used to prepare 2-fluoro-4-nitrophenylhydrazine hydrochloride, is also a known compound and can be prepared according to the method of J. B. Dickey, U.S. Pat. No. 2,436,100.

The following examples further illustrate the method for synthesis of compounds of this invention. All parts are by weight and all temperatures in degrees centigrade.

EXAMPLE 1

Preparation of 3-Chloro-2-(4-chloro-2-fluorophenyl)-4,5,6,7-tetrahydro-2H-indazole

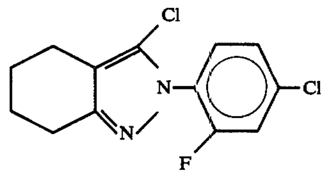

a. Preparation of 4-Chloro-2-fluoroaniline

Seventy-one parts of liquid chlorine were added to a solution of 140 parts of 2'-fluoroacetanilide in 500 parts glacial acetic acid, during one hour, at 25°-27°, with icewater cooling. While stirring for 4 hours at 25°-27°, 4'-chloro-2'-fluoroacetanilide precipitated. After collecting the product by filtration, the filtrate was poured over 2000 parts of ice. The resulting second portion of precipitated product was collected by filtration, combined with the first portion and recrystallized from 700 parts of methanol at −45° to yield 119 parts of 4'-chloro-2'-fluoroacetanilide as white crystals melting at 152°-155°.

A mixture of 119 parts of 4'-chloro-2'-fluoroacetanilide in 475 parts of ethanol and 200 parts of 37% hydrochloric acid was refluxed for 17 hours and the solvent removed under a reduced pressure of 300 mm. Hg to yield the moist, solid hydrochloride salt of 4-chloro-2-fluoroaniline.

The moist, solid hydrochloride salt of 4-chloro-2-fluoroaniline was cooled to 10° in an ice-acetone bath and 50% aqueous sodium hydroxide was added dropwise, with stirring, until pH 11 was obtained. The resulting two-phase mixture was extracted four times; 500 parts of methylene chloride was used for each extraction. The combined organic extracts were dried with anhydrous sodium sulfate and the solvent removed under a reduced pressure of 300 mm. Hg to leave 89 parts of light brown, oily 4-chloro-2-fluoroaniline, $n_D^{25} = 1.5541$.

b. Preparation of 4-Chloro-2-fluorophenylhydrazine Hydrochloride 20.0 Parts of 4-chloro-2-fluoroaniline was dissolved in 80 parts of water and 34 parts of concentrated hydrochloric acid. The solution was cooled to 0°-10° and 32.2 parts of 30% sodium nitrite was added dropwise maintaining the temperature of the reaction between 0°-10°. After the addition of nitrite was completed, the solution was stirred for thirty minutes at 0°-10°. Excess nitrite was destroyed by addition of small amounts of sulfamic acid. When a negative test with sulfone reagent was obtained, the diazonium salt was ready for reduction. For a description of the sulfone test, see H. E. Fierz-David et al., *Fundamental Processes of Dye Chemistry* translated from 5th Austrian Ed. by P. W. Wittam, Interscience Publishers, Inc., New York, 1949, p. 243.

In a separate vessel 35.4 parts of sodium bisulfite and 32.2 parts of 30% sodium hydroxide solution were dissolved in 140 parts of water. The solution was heated to 40°. The diazonium salt was added to the bisulfite solution over a period of about 1 hour. The mixture was heated to 70° and 0.3 parts of sodium hydrosulfite was added. The pH was adjusted to 1.2 with 30 parts of concentrated hydrochloric acid; then an additional 90 parts of concentrated hydrochloric acid was added. The reaction mixture was heated for 1.5 hours at 70°, cooled slowly, and stirred overnight at room temperature.

Purification was achieved by heating the reaction mixture to 70° and filtering. The filtrate was cooled to 10° at which time 4-chloro-2-fluorophenylhydrazine hydrochloride precipitated. This product was filtered and dried to yield 10.7 parts of yellow crystalline solid, m.p. 223°.

c. Preparation of 2-(4-Chloro-2-fluorophenyl)-1,2,4,5,6,7-hexahydro-3H-indazol-3-one 15.8 Parts of 2-fluoro-4-chlorophenylhydrazine hydrochloride, 13 parts of 2-carbethoxycyclohexanone (purchased from Aldrich Chemical Company), and 8.1 parts of triethylamine were dissolved in 100 parts of ethanol. The reactants were heated at reflux for twenty-four hours. The crude reaction mass was poured into 1000 parts of water. The resulting gummy product solidified and was filtered and dried to yield 16.1 parts of crude product with m.p. 163°-170°. This material was used without further purification in the next step.

By substituting 4-chlorophenylhydrazine hydrochloride in the above procedure for 4-chloro-2fluorophenylhydrazine hydrochloride, 2-(4-chlorophenyl)-1,2,4,5,6,7-hexahydro-3H-indazol-3-one was prepared, m.p. 183.5°-185° (Lit 186°-187°, Chem. Abs., 67, 11452h).

d. Preparation of 3-Chloro-2-(4-chloro-2-fluorophenyl)-4,5,6,7-tetrahydro-2H-indazole 10.0 Parts of 2-(4-chloro-2-fluorophenyl)-1,2,4,5,6,7-hexahydro-3H-indazol-3-one and 7.3 parts of phosphorous oxychloride were mixed and heated to 130°-150° for six hours. The reaction mixture was dissolved in 100 parts of chloroform. The organic solution containing the product was washed successively with three portions of 25 parts each of 10% sodium hydroxide and then washed with 50 parts water. The chloroform solution was dried with 2-10 parts of anhydrous sodium sulfate and then filtered. The solvent was removed under a reduced pressure on a rotary evaporator. The resulting thick oil was purified by sublimation at 100°-120° at 0.5-1.5 mm. pressure to yield 7.8 parts of white crystalline material with m.p. 88°-89.5°.

Preparations of other novel anilines used in this invention are as follows:

PREPARATION OF 4-BROMO-2-FLUOROANILINE

160 Parts of solid N-bromosuccinimide were added in portions over a 2-hour period to a solution of 100 parts of 2-fluoroaniline in 400 parts of methylene chloride cooled to 0°. After stirring for 20 minutes, the dark red mixture was washed four times; 200 parts of cold water were used for each washing. The red organic phase was dried with anhydrous sodium sulfate and evaporated under 300 mm. Hg to 164 parts of brown, oily 4-bromo-2-fluoroaniline, $n_D^{25}$: 1.5885.

PREPARATION OF 4-AMINO-3-FLUOROBENZONITRILE 6.8 Parts of 4-bromo-2-fluoroaniline were dissolved in 75 parts of N-methylpyrrolidone. This solution was treated with 4.2 parts of cuprous cyanide. The reaction mixture was heated to 190° for 2 hours. The reaction mass was poured onto a mixture of 200 parts of ice and 15 parts of sodium cyanide. This mixture was then heated on a steam bath for 2 hours at 60°-70°. This aqueous solution was then extracted with four 100 ml portions of toluene. The toluene extracts were combined and washed with four 300-ml portions of water followed by 100 ml of saturated NaCl. The toluene solution of the product was dried over sodium sulfate and stripped to give 2.6 parts of the desired product, m.p. 71°-73°.

Using the procedure of Example 1 with 2-carbethoxycyclohexanone, the appropriate hydrazine acid salt and phosphorous oxychloride, the following compounds of Formula I are prepared:

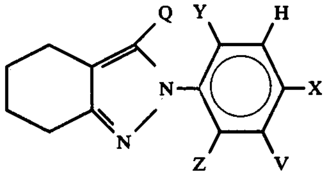

| Q | Y | X | V | Z | m.p.° C |
|---|---|---|---|---|---|
| Cl | H | Cl | H | H | 81-84° |
| Cl | H | Br | H | H | 86-88° |
| Cl | H | $NO_2$ | H | H | 103-105° |
| Cl | H | $CH_3O$ | H | H | oil, ir bands (760 $cm^{-1}$, 835 $cm^{-1}$) |
| Cl | Cl | Cl | H | H | oil, ir bands (735 $cm^{-1}$, 820 $cm^{-1}$) |
| Cl | H | Cl | Cl | H | 69-71° |
| Cl | H | F | Cl | H | 70-72° |
| Cl | F | Br | H | H | 86-88° |
| Cl | F | $CH_3O$ | H | H | |
| Cl | F | $NO_2$ | H | H | 108-109.5° |
| Cl | F | CN | H | H | 113-116° |
| Cl | F | F | H | H | $n_D^{25} = 1.5587$ |
| Cl | Cl | Cl | Cl | H | 101-105° |
| Cl | H | Br | Cl | H | |
| Cl | H | CN | H | H | 104-106.5° |
| Cl | H | F | Cl | H | 70-72° |
| Cl | H | F | H | H | 35-37° |
| Cl | Cl | Br | H | H | 78-79° |
| Cl | F | F | F | H | |
| Cl | F | I | H | H | 83.5-87° |
| Cl | Cl | Cl | H | F | 93.5-101° |
| Cl | F | F | H | F | 57.5-62° |
| Cl | Cl | F | H | H | 75-78.5° |
| Cl | H | I | H | H | 91-103° |
| Cl | Cl | Cl | $OCH_3$ | H | 107-110° |
| Cl | F | Cl | Cl | H | |

Using the procedure of Example 1 with a methyl substituted 2-carbethoxycyclohexanone, the appropriate aryl hydrazine, and phosphorous oxychloride, the following compounds may be prepared:

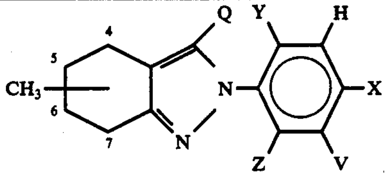

| $R_1$ | Q | Y | X | V | Z | m.p. ° C |
|---|---|---|---|---|---|---|
| 7-$CH_3$— | Cl | F | F | F | H | |
| 7-$CH_3$— | Cl | F | F | H | F | |
| 7-$CH_3$— | Cl | F | Cl | H | H | 58-61.5° |

-continued

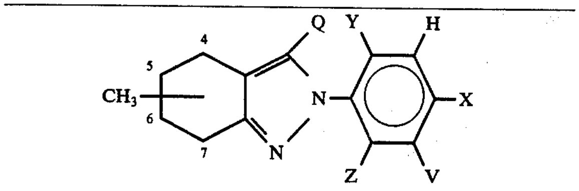

| $R_1$ | Q | Y | X | V | Z | m.p. ° C |
|---|---|---|---|---|---|---|
| 7-$CH_3$— | Cl | F | Br | H | H | |
| 7-$CH_3$— | Cl | F | F | H | H | |
| 7-$CH_3$— | Cl | H | Cl | H | H | ir bands 1570, 835 $cm^{-1}$ |
| 7-$CH_3$— | Cl | H | $OCH_3$ | H | H | $n_D^{25}$ 1.5839 |
| 7-$CH_3$— | Cl | F | F | H | F | |
| 5-$CH_3$— | Cl | F | Cl | H | H | 85-88° |
| 5-$CH_3$— | Cl | H | Cl | H | H | 96.5-99° |
| 6-$CH_3$— | Cl | F | Cl | H | H | 43.5-44.5° |
| 6-$CH_3$ | Cl | F | I | H | H | ir bands 1600, 870, 825 $cm^{-1}$ |
| 6-$CH_3$— | Cl | H | Cl | Cl | H | |
| 6-$CH_3$— | Cl | H | Cl | H | H | 75-76° |
| 6-$CH_3$— | Cl | H | CN | H | H | 103-105° |
| 6-$CH_3$— | Cl | H | $OCH_3$ | H | H | $n_D^{25}$=1.5839 |
| 6-$CH_3$— | Cl | H | $NO_2$ | H | H | 89-91.5° |
| 4-$CH_3$— / 6-$CH_3$— | Cl | H | Cl | H | H | 47.5-52° for mixture |
| 4-$CH_3$ / 6-$CH_3$ | Cl | F | Cl | H | H | 41-45° for mixture |
| 6-$CH_3$— | Cl | F | I | H | H | |
| 6-$CH_3$— | Cl | Cl | Cl | $OCH_3$ | H | |

EXAMPLE 2

Preparation of 3-Chloro-2-(4-chlorophenyl)-2,4,5,6,7,8-hexahydrocycloheptapyrazole

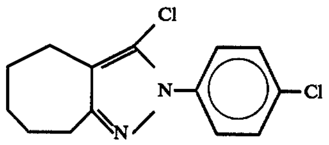

By substituting 2-carbethoxycycloheptanone [prepared by the method of G. Stork, et al., J. Am. Chem. Soc., 85, 207 (1963)] and p-chlorophenylhydrazine hydrochloride (available from Aldrich Chemical Company) in the procedure of Example 1(c), 2-(4-chlorophenyl)-1,4,5,6,7,8-hexahydrocycloheptapyrazol-3(2H)-one (m.p. 224°-225° ) was prepared. By reacting this pyrazolone with phosphorous oxychloride according to the procedure of Example 1(d), 3-chloro-2-(4-chlorophenyl)-2,4,6,7,8-hexahydrocycloheptapyrazole (m.p. 59°-61° ) was obtained.

Following the procedure of Example 2, using the appropriate aryl hydrazine hydrochloride (for p-chlorophenylhydrazine hydrochloride) and phosphorous oxychloride, the following compounds of Formula I may be prepared:

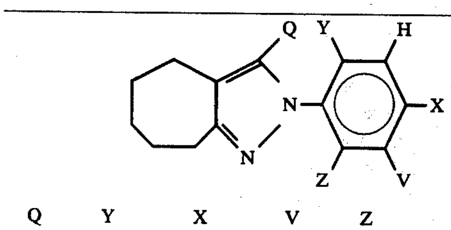

| Q | Y | X | V | Z | m.p.° C |
|---|---|---|---|---|---|
| Cl | F | Br | H | H | 82.5-83.0° |

-continued

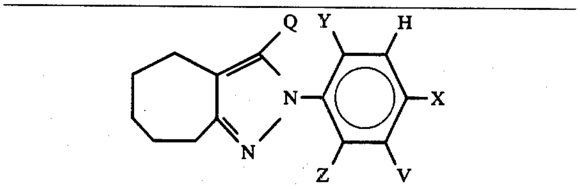

| Q | Y | X | V | Z | m.p.° C |
|---|---|---|---|---|---|
| Cl | F | F | H | H | |
| Cl | F | $OCH_3$ | H | H | |
| Cl | F | CN | H | H | |
| Cl | F | $NO_2$ | H | H | |
| Cl | F | Cl | H | H | 68-69.5° |
| Cl | H | CN | H | H | 95-102° |
| Cl | H | Br | H | H | 53-55° |
| Cl | F | I | H | H | |
| Br | F | Cl | H | H | |
| Br | F | Br | H | H | |

EXAMPLE 3 a. Preparation of 2-(4-chloro-2-fluorophenyl)-1,4,5,6-tetrahydrocyclopentapyrazol-3(2H)-one 7.5 Parts of 4-chloro-2-fluorophenylhydrazine and 6.6 parts of methyl 2-oxocyclopentanecarboxylate (purchased from Aldrich Chemical Company) were dissolved in 200 parts toluene. The reactants were heated at reflux for 1-2 hours removing water that was formed. The reaction mixture was cooled to 100° C., and a solution of 5.0 parts of sodium methoxide dissolved in 25 parts methanol was added dropwise, removing methanol as its azeotrope with toluene. The reaction mixture was heated until the internal temperature reached 110°. The reaction was then cooled and poured into 200 parts ice water. The organic layer was separated, and the aqueous layer was washed twice with diethyl ether. Cold, dilute hydrochloric acid was added, with stirring, to the aqueous layer until pH 2 was reached. The resulting oily product solidified and was filtered, dried and recrystallized from acetonitrile to yield 3.3 parts of tan crystalline material, m.p. 157°-160°.

Alternatively, the above pyrazolone was prepared by the following procedure. 16.0 Parts of 4-chloro-2-fluorophenylhydrazine and 14.2 parts of methyl 2-oxocyclopentanecarboxylate were dissolved in 100 parts of benzene. The reaction mixture was refluxed for 1-2 hours removing water that was formed. The reaction mixture was cooled, and the solvent was removed under reduced pressure on a rotary evaporator. The resulting brown oil was dissolved in 150 parts of anhydrous tetrahydrofuran and the solution was cooled to 0° under a nitrogen atmosphere. To the cold reaction solution, 2 equivalents of n-butyllithium in hexane (purchased from Foote Mineral Company) were added at such a rate that internal temperature was maintained at 0°-5°. The reaction mixture was allowed to warm to ambient temperature, then heated at reflux for 18 hours. The reaction mixture was cooled and poured into 200 parts ice water. The organic layer was separated, and the aqueous layer was washed twice with diethyl ether. Cold, dilute hydrochloric acid was added to the aqueous layer until pH 2 was attained. The resulting oily product solidified, and was filtered, dried, and recrystallized from acetonitrile to yield 17.5 parts of tan crystalline material, m.p. 165°-167°.

By substituting 4-chlorophenylhydrazine in the former procedure for 4-chloro-2-fluorophenylhydrazine, 2-(4-chlorophenyl)-1,4,5,6-tetrahydrocyclopentapyrazol-3(2H)-one was prepared, m.p. 193.5°-195°.

b. Preparation of 3-chloro-2-(4-chloro-2-fluorophenyl)-2,4,5,6-tetrahydrocyclopentapyrazole By reacting 2-(4-chloro-2-fluorophenyl)-1,4,5,6-tetrahydrocyclopentapyrazol-3(2H)-one with phosphorous oxychloride according to the procedure of Example 1(d), 3-chloro-2-(4-chloro-2-fluorophenyl)-2,4,5,6-tetrahydrocyclopentapyrazole (m.p. 102°-104° ) was obtained.

Using the procedure of Example 3 with the appropriate methylsubstituted 2-oxocyclopentanecarboxylate, the appropriate hydrazine and phosphorous oxychloride, the following compounds of Formula I can be prepared:

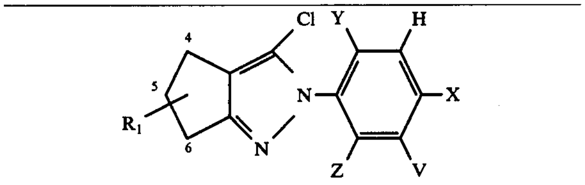

| $R_1$ | Y | X | V | Z | m.p.° C |
|---|---|---|---|---|---|
| H | H | Cl | H | H | 114.5-117° |
| H | Cl | Cl | H | H | 119-123° |
| H | H | Br | H | H | 120-121° |
| H | Cl | Br | H | H | 113-119° |
| H | F | Br | H | H | 105-106.5° |
| H | F | F | H | H | 110-119° |
| H | H | F | H | H | 57-60° |
| H | F | F | H | F | |
| H | Cl | Cl | Cl | H | |
| H | H | Br | Cl | H | |
| H | F | $CH_3O$ | H | H | |
| H | F | $NO_2$ | H | H | |
| H | F | CN | H | H | |
| H | H | $CH_3O$ | H | H | |
| H | H | $NO_2$ | H | H | |
| H | H | CN | H | H | 126.5-128° |
| H | H | Cl | Cl | H | 95-98° |
| H | H | F | Cl | H | |
| 4-$CH_3$ | F | Cl | H | H | |
| 4-$CH_3$ | H | Cl | H | H | |
| { 5-$CH_3$ | F | Cl | H | H | } ir bands 1590, 905, 990 $cm^{-1}$ |
| { 4-$CH_3$ | F | Cl | H | H | } |
| 5-$CH_3$ | H | Cl | H | H | |
| 6-$CH_3$ | H | Cl | H | H | |
| 6-$CH_3$ | F | Cl | H | H | 88-93° |
| H | F | I | H | H | |
| H | Cl | Cl | $OCH_3$ | H | |
| 7-$CH_3$ | F | Cl | H | H | |

EXAMPLE 4

Preparation of 3-bromo-2-(4-chlorophenyl)-4,5,6,7-tetrahydro-2H-indazole

To 5.0 parts of 2-(4-chlorophenyl)-1,2,4,5,6,7-hexahydro-3H-indazol-3-one [from Example 1(c)] with 3.0 parts of N,N-diethylaniline and 5.0 parts of dimethylformamide under nitrogen atmosphere was added 6.3 parts of phosphorous oxybromide. The mixture was heated to 130°-170° for two hours. After cooling to room temperature, the reaction mixture was extracted with 100 parts of diethyl ether, washed with water, dried over anhydrous magnesium sulfate and concentrated on a rotary evaporator. Recrystallization from methanol/water gave 2.7 parts of product, m.p. 101°-102°.

Using the procedure of Example 4 with the appropriate annelated pyrazolones 3, which can be prepared by a method taught in Example 1 or Example 3, the following compounds can be prepared:

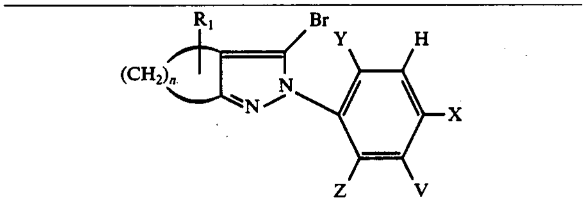

| n | $R_1$ | Y | X | V | Z | mp° C |
|---|---|---|---|---|---|---|
| 3 | H | F | Cl | H | H | 106-110° |
| 3 | H | H | Cl | Cl | H | |
| 3 | H | H | Cl | H | H | 109-112° |
| 3 | H | Cl | Cl | H | H | |
| 3 | H | F | F | H | H | |
| 3 | H | F | F | H | F | |
| 3 | H | F | Br | H | H | |
| 3 | 4-$CH_3$ | F | Cl | H | H | |
| 3 | 6-$CH_3$ | F | Cl | H | H | |
| 3 | H | F | $CH_3O$ | H | H | |
| 3 | H | F | $NO_2$ | H | H | |
| 3 | H | F | CN | H | H | |
| 4 | H | F | Cl | H | H | 95-98° |
| 4 | H | F | Br | H | H | |
| 4 | H | F | F | H | H | |
| 4 | H | Cl | Cl | H | H | 101-102° |
| 4 | H | F | F | H | F | |
| 4 | H | F | $CH_3O$ | H | H | |
| 4 | H | F | $NO_2$ | H | H | |
| 4 | H | F | CN | H | H | |
| 4 | H | H | $NO_2$ | H | H | |
| 4 | H | H | Br | H | H | 84-87° |
| 4 | H | H | F | H | H | 70-73° |
| 4 | H | H | $CH_3O$ | H | H | |
| 4 | H | H | CN | H | H | |
| 4 | H | H | Cl | Cl | H | |
| 4 | 5-$CH_3$ | F | Cl | H | H | |
| 4 | H | F | I | H | H | |
| 4 | H | Cl | Cl | $OCH_3$ | H | |
| 4 | H | F | F | F | H | |
| 4 | 7-$CH_3$ | F | Cl | H | H | |
| 4 | H | H | $NO_2$ | H | H | |
| 5 | H | F | Cl | H | H | 59-60° |
| 5 | H | H | Cl | H | H | |
| 5 | H | H | $CH_3O$ | H | H | |

EXAMPLE 5

Preparation of 3-iodo-2-(4-chlorophenyl)-4,5,6,7-tetrahydro-2H-indazole a. Preparation of 3-amino-2-(4-chlorophenyl)-4,5,6,7-tetrahydro-2H-indazole A mixture of 3.6 parts of 4-chlorophenylhydrazine and 2.0 parts of triethylamine in 20.0 parts of toluene was stirred at room temperature for fifteen minutes. To the mixture was added 2.5 parts of 2-cyanocyclohexanone, prepared from commercial 2-chlorocyclohexanone and potassium cyanide [von R. E. Meyer, Helv. Chim. Acta., 16, 1291 (1933)], and a few drops of acetic acid. After refluxing for two hours, followed by stirring at room temperature overnight, the reaction mixture was evaporated to remove toluene and was treated with water, extracted with diethyl ether, dried over anhydrous magnesium sulfate and concentrated. Recrystallization from ethanol/water gave 2.6 parts of the compound, m.p. 140°-142°.

b. Preparation of 3-iodo-2-(4-chlorophenyl)-4,5,6,7-tetrahydro-2H-indazole

To 2.5 parts of 3-amino-2-(4-chlorophenyl)-4,5,6,7-tetrahydro-2H-indazole in 2.5 parts of conc. sulfuric acid and 15 parts of water cooled to 0° was added dropwise a solution of 0.8 parts of sodium nitrite in 5.0 parts of water and the mixture was stirred for one and a half hours. Excess nitrous acid was destroyed using sulfamic acid. 1.7 Parts of potassium iodide in 5.0 parts of water was then added slowly to the diazonium solution. After stirring at 0°–25° for two hours, the precipitate was collected by filtration and dried. Recrystallization from ethanol/water gave 1.7 parts of the product, m.p. 83° (decomp.).

Using the method of Example 5 with the appropriate α-cyanoketone which is conveniently prepared by reacting the appropriate α-chlorocyclohexaone or α-chlorocyclopentanone with sodium cyanide. According to the method of Meyer, Helv. Chim. Acta., 16, 1291 (1933), the following compounds of Formula I can be prepared:

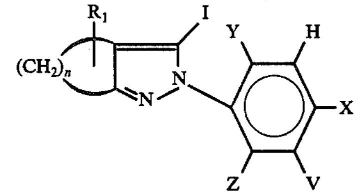

| n | $R_1$ | Y | X | V | Z | m.p. ° C |
|---|---|---|---|---|---|---|
| 3 | H | F | Cl | H | H | 106° d |
| 3 | H | H | Cl | H | H | |
| 3 | H | F | Br | H | H | |
| 3 | H | F | F | H | H | |
| 3 | H | F | $CH_3O$ | H | H | |
| 3 | H | F | $NO_2$ | H | H | |
| 3 | H | F | CN | H | H | |
| 4 | H | F | Cl | H | H | 133–135° |
| 4 | H | F | Br | H | H | |
| 4 | H | F | F | H | H | |
| 4 | H | H | $CH_3O$ | H | H | |
| 4 | H | H | $NO_2$ | H | H | |
| 4 | H | H | CN | H | H | |
| 4 | H | F | I | H | H | |

EXAMPLE 6

Preparation of 3-fluoro-2-(4-fluorophenyl)-4,5,6,7-tetrahydro-2H-indazole a. Preparation of 2-(4-chloro-2-fluorophenyl)-4,5,6,7-tetrahydro-2H-indazole-3-diazonium fluoborate To 50 parts of 48% fluoboric acid at 0°–5° was added simultaneously a solution of 2.5 parts of sodium nitrite in 10 parts of water and a suspension of 8.7 parts of 3-amino-2-(4-chloro-2-fluorophenyl)-4,5,6,7-tetrahydro-2H-indazole in 30 parts of acetic acid in small portions, so that the mixture always contained an excess of nitrite [E. D. Bergmann, S. Berkovic and R. Ikan, J. Am. Chem. Soc. 78, 6037 (1956)]. After the addition, the reaction mixture was stirred at 0°–10° for one hour and 10°–25° for half an hour. Excess nitrous acid was destroyed using sulfamic acid. The precipitates were collected, washed with water, ethyl ether and dried, yielding 9.0 parts of the product. The ir indicated that no amino compound was left and it showed $-N_2-$ absorption at 2200 $cm^{-1}$. The compound was used without further recrystallization.

b. Preparation of 3-fluoro-2-(4-chloro-2-fluorophenyl)-4,5,6,7-tetrahydro-2H-indazole A mixture of 9.0 parts of 2-(4-chloro-3-fluorophenyl)-4,5,6,7-tetrahydro-2H-indazole-3-diazonium fluoborate and 10 parts of potassium fluoride in 100 parts of fluoboric acid was photolyzed by a 200 W Hanovia high pressure mercury-vapor lamp at 0° for one hour and at room temperature for fifteen hours. The reaction mixture was extracted with ether, washed with water, dried over anhydrous magnesium sulfate and concentrated. The desired product was isolated by dry-column chromatography (silica gel eluted with methylene chloride), preparative thin layer chromatography (silica gel developed with 5 parts of $Et_2O$: 100 parts of hexane) and preparative gas chromatography (15% OV-17 on 80/100 mesh chromosorb W HP at 250°). The product was shown to be pure by GC and was analyzed by mass spectroscopy ($M^+$= 268 and $^{m}/e$ + 240 due to the loss of $C_2H_4$). nmr δ 1.5 (m, 4H), 2.0–2.2 (2t, 4H), and 7.0 (m, 3H).

Using the method of Example 6 with the appropriate 3-amino compound (Example 5a), the following compounds can be prepared:

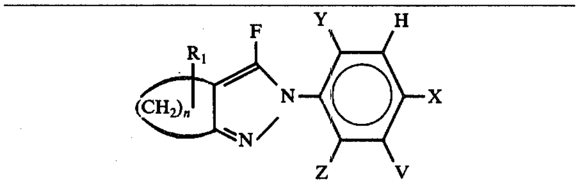

| n | $R_1$ | Y | X | V | Z |
|---|---|---|---|---|---|
| 3 | H | F | Cl | H | H |
| 3 | H | H | Cl | H | H |
| 3 | H | F | Br | H | H |
| 3 | H | F | CN | H | H |
| 3 | H | F | $CH_3O$ | H | H |
| 3 | H | H | Br | H | H |
| 3 | H | H | CN | H | H |
| 4 | H | H | Cl | H | H |
| 4 | H | F | Br | H | H |
| 4 | H | F | CN | H | H |
| 4 | H | F | $CH_3O$ | H | H |
| 4 | H | H | Br | H | H |
| 4 | H | F | $NO_2$ | H | H |
| 4 | H | F | I | H | H |

FORMULATIONS

Useful formulations of the compounds of Formula I include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.05% to 99% by weight of active ingredient(s) and at least one of (a) about 0.1% to 20% surfactant(s) and (b) about 1% to 99.95% solid or liquid diluents(s). More specifically, they will usually contain these ingredients in the following approximate proportions:

| | Percent by Weight | | |
|---|---|---|---|
| | Active Ingredient | Diluent(s) | Surfactant(s) |
| Wettable Powders | 5–90 | 1–94 | 1–10 |
| Oil Suspensions, Emulsions, Solutions (including Emulsifiable Concentrates) | 5–50 | 40–95 | 0–15 |
| Aqueous Suspensions | 5–50 | 40–94 | 1–20 |
| Dusts | 0.05–25 | 70–99.95 | 0–5 |
| Granules and Pellets | 0.05–95 | 1–99.95 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd. Edn., Dorland Books, Caldwell, N.J. Suitable diluents include finely divided or granular solids classified as attapulgites, botanicals, calcites, diatomites, dolomites, gypsum, kaolinites, limestones, mica, montmorillonoids, phosphates, pyrophyllites, sulfur, sand, talcs, tripolites, vermiculite, and synthetics. These synthetics can include precipitated, hydrated silicon dioxide, precipitated, hydrated calcium silicate, precipitated calcium carbonate and synthetic organics. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers 1975 Annual," MC Publ. Corp., Ridgewood, New Jersey, as well as Sisely and Wood, "Encyclopedia of Surface Active Agents," Chemical Publ. Co., New York, 1964, list surfactants and recommended uses. All formulations can contain minor amounts of additives to reduce foam, caking, corrosion, microbiological growth, etc., or to mark visually the area that has been treated.

It is sometimes desirable to add ingredients to reduce the volatility of some of the compounds of this invention. Those additives can include film forming materials such as polyvinylpyrrolidones of molecular weights from about 20,000 to about 100,000; polyvinylalcohols of molecular weights from about 20,000 to about 150,000; and polyoxyethylenes of molecular weights from about 100,000 to about $6 \times 10^6$. These are a few examples of film forming additives. Any material which forms a film over solid active ingredient in the formulation preparation or a film over the active when sprayed and dried from a liquid formulation can be used. Other methods to reduce volatility may include the incorporation of the compounds of this invention into resins, waxes, gums, rubbers, or the like, and then preparing formulations, as has been described above, for these combinations.

Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

Granules may be made in several ways. For example, the active ingredient may be sprayed onto preformed granular carriers. Suitable preformed granular carriers include those suitable diluents listed earlier having a particle size range from USS Sieve No. 200 (74 microns) to USS Sieve No. 10 (2000 microns). The preferred particle size is from USS Sieve No. 140 (105 micron) to USS Sieve No. 20 (840 microns). Depending upon the nature of the carrier, the active ingredient may remain on the surface of the carrier or be absorbed into the carrier. Usually when the active ingredient remains on the surface of the carrier, a binding agent is used to hold the active ingredient on the surface. The binding agent should bind the active ingredient to the surface well enough so that not more than 10% of the active is removed during normal shipping and handling operations. Suitable binding agents include materials which are at least partially soluble in any liquid used in the manufacture of the granules and which adhere to the granular surface. Water-soluble binders are preferred. Suitable binders include, but are not limited to, water-soluble polymers such as polyvinylalcohols of molecular weights from about 20,000 to about 150,000; polyvinylpyrrolidones of molecular weights from about 20,000 to about 100,000; and polyoxyethylenes of molecular weights from about 100,000 to about $6 \times 10^6$. Other suitable binders include, ligninsulfonates, starches, sugars, and certain surface active agents listed in McCutcheons' Detergents and Emulsifiers 1975 Annual", M C Publ. Corp., Ridgewood, New Jersey.

The active may be sprayed as a solution in a suitable solvent, which may or may not be removed from the formulation. If the active ingredient is a liquid, it may be sprayed onto or mixed with the carrier directly. If it is a solid, it may be melted and applied directly as a liquid. If very low strength granules are desired, the active may be vaporized onto the carrier. Granules may also be prepared by agglomeration techniques. For example, the active ingredient and a finely divided solid diluent may be mixed and agglomerated by techniques known in the art such as spraying with a liquid in a fluidized bed or pan granulator. The active ingredient and diluent may also be mixed with other formulation ingredients and pelletized. The pellets may then be crushed to a desired granular size. Pellets may be made by agglomeration techniques. See J. E. Browning, "Agglomeration," *Chemical Engineering,* Dec. 4, 1967, pp. 147ff. and "Perry's Chemical Engineer's Handbook," 4th, Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, March 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3 Line 66 through Col. 5 Line 17 and Examples 1–4.

G. C. Klingman, "Weed Control as a Science," John Wiley & Sons, Inc., New York, 1961 pp. 81–96.

J. D. Fryer and S. A. Evans, "Weed Control Handbook," 5th Edn. Blackwell Scientific Publications, Oxford, 1968, pp. 101–103.

EXAMPLE 7

| Granule | |
|---|---|
| 3-chloro-2-(4-chlorophenyl)-4,5,6,7-tetrahydro-2H-indazole | 10% |
| attapulgite granules (low volatile matter, 0.71–0.30 mm. diameter; i.e., U.S.S. #25–50 mesh sieve size) | 90% |

The active ingredient is warmed to approximately 90° and sprayed upon dedusted and pre-warmed attapulgite granules in a double cone blender. The granules are then allowed to cool and are packaged.

EXAMPLE 8

| Solution | |
|---|---|
| 3-chloro-2-(2,4-difluorophenyl)-4,5,6,7- | 20% |

-continued

| Solution | |
|---|---|
| tetrahydro-2H-indazole | |
| dimethylformamide | 80% |

The ingredients are combined and stirred to produce a solution, which can be used for low-volume applications.

EXAMPLE 9

| Extruded Pellet | |
|---|---|
| 3-chloro-2-(4-chloro-2-fluorophenyl)-4,5,6,7-tetrahydro-2H-indazole | 1% |
| anhydrous sodium sulfate | 10% |
| crude calcium ligninsulfonate | 5% |
| sodium alkylnaphthalenesulfonate | 1% |
| polyoxyethylene (4 × $10^6$ average molecular wt.) | 1% |
| calcium/magnesium bentonite | 82% |

The ingredients are blended, hammer milled and then moistened with about 12% water. The mixture is extruded as cylinders about 3mm diameter which are cut to produce pellets about 3 mm long. These may be used directly after drying, or the dried pellets may be crushed to pass a U.S.S. No. 20 sieve (0.84 mm. openings). The granules held on a U.S.S. No. 40 sieve (0.42 mm openings) may be packaged for use and the fines recycled. All compounds of this invention may be formulated in this manner.

EXAMPLE 10

| Emulsifiable Concentrate | |
|---|---|
| 3-chloro-2-(4-chlorophenyl)-4,5,6,7-tetrahydro-2H-indazole | 25% |
| blend of oil soluble sulfonates and polyoxyethylene ethers | 4% |
| xylene | 71% |

The ingredients are combined and stirred until solution is complete. A fine screen filter is included in packaging operation to insure the absence of any extraneous undissolved material in the product.

EXAMPLE 11

| Aqueous Suspension | |
|---|---|
| 3-chloro-2-(4-chlorophenyl)-4,5,6,7-tetrahydro-2H-indazole | 50.0% |
| polyacrylic acid thickener | 0.3% |
| dodecylphenol polyethylene glycol ether | 0.5% |
| disodium phosphate | 1.0% |
| monosodium phosphate | 0.5% |
| polyvinylalcohol | 1.0% |
| pentachlorophenol | 0.4% |
| water | 46.3% |

The ingredients are ground together in a sand mill to produce particles essentially all under five microns in

EXAMPLE 12

| Wettable Powder | |
|---|---|
| 3-chloro-2-(4-chloro-2-fluorophenyl)-4,5,6,7-tetrahydro-2H-indazole | 50% |
| sodium alkylnaphthalenesulfonate | 2% |
| sodium ligninsulfonate | 2% |
| synthetic amorphous silica | 3% |

-continued

| Wettable Powder | |
|---|---|
| kaolinite | 43% |

The ingredients are thoroughly blended, passed through an air mill to produce an average particle size under 15 microns, reblended, and sifted through a U.S.S. No. 50 sieve (0.3 mm. opening) before packaging.

EXAMPLE 13

| High-Strength Concentrate | |
|---|---|
| 3-chloro-2-(4-chloro-2-fluorophenyl)-4,5,6,7-tetrahydro-2H-indazole | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE 14

| Low Strength Granule | |
|---|---|
| 3-chloro-2-(4-chloro-2-fluorophenyl)-4,5,6,7-tetrahydro-2H-indazole | 0.5% |
| polyvinylpyrrolidone | 1% |
| attapulgite granules (low volatile matter; 0.59–0.25 mm., i.e. USS#30–60 mesh size) | 98.5% |

Forty grams of a solution containing 2.5% 3-chloro-2-(4-chloro-2-fluorophenyl)-4,5,6,7-tetrahydro-2H-indazole and 5% polyvinylpyrrolidone dissolved in methyl alcohol are slowly atomized onto a fluidized bed of attapulgite granules (197 gm). Fluidization of the granules is continued after atomization is complete and until all the methyl alcohol is evaporated from the granules. The granules are packaged for use.

EXAMPLE 15

| Extruded Pellet | |
|---|---|
| 3-chloro-2-(4-chlorophenyl) 2,4,5,6-tetrahydrocyclopentapyrazole | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and moistened with about 10–12% water. The mixture is then extruded as cylinders about 3 mm in diameter which are cut to be about 3 mm. long. These pellets may be used directly after drying or the dried pellets may be crushed to pass a USS #20 sieve (0.84 mm opening). The pellets retained on a USS #40 sieve (0.42 mm openings) may be packaged for use and the fines recycled.

EXAMPLE 16

| Granule: | |
|---|---|
| 3-chloro-2-(4-chloro-2-fluorophenyl) 2,4,5,6-tetrahydrocyclopentapyrazole | 2% |
| attapulgite granules (low volatile matter; 0.71–0.30 mm., i.e. USS#25–50 mesh sieves) | 98% |

The active ingredient is warmed to approximately 110° and sprayed upon the dedusted and prewarmed granules in a double cone blender. The granules are allowed to cool and are packaged for use.

EXAMPLE 17

| Low Strength Granule | |
|---|---|
| 3-chloro-2-(4-chlorophenyl)2,4,5,6-tetrahydrocyclopentapyrazole | 0.2% |
| anhydrous sodium sulfate | 10% |
| crude calcium ligninsulfonate | 5% |
| sodium alkylnaphthalenesulfonate | 1% |
| finely divided attapulgite clay | 83.8% |

The ingredients are blended, hammer milled and placed in a fluidized bed granulator. Water is aspirated into the fluidized bed of powder until small granules are formed. Water aspiration is then stopped but fluidization is continued to dry the formed granules. The granules are removed from the granulator and screened to pass a USS #20 sieve (0.84 mm opening). Granules retained on a USS #40 sieve (0.42 mm opening), are packaged for use. Granules larger than 0.84 mm are ground and recycled. Fines smaller than 0.42 mm are also recycled.

EXAMPLE 18

| Extruded Pellet | |
|---|---|
| 3-chloro-2-(4-chlorophenyl)-4,5,6,7-tetrahydro-2H-indazole | 0.1% |
| anhydrous sodium sulfate | 10% |
| crude calcium ligninsulfonate | 5% |
| sodium alkylnaphthalenesulfonate | 1% |
| polyoxyethylene (4 × $10^6$ average molecular wt.) | 1% |
| calcium/magnesium bentonite | 82.9% |

The ingredients are blended, hammer milled and then moistened with about 12% water. The moist mixture is extruded as cylinders about 1 mm in diameter and about 2 mm. long. These small pellets are dried and packaged. They are applied directly.

EXAMPLE 19

| Low Strength Granule | |
|---|---|
| 3-chloro-2-(4-chloro-2-fluorophenyl)-4,5,6,7-tetrahydro-2H-indazole | 0.05% |
| dimethylformamide | 5% |
| attapulgite granules (low volatile matter; 0.59–0.25 mm. i.e. USS #30-60 mesh size) | 94.95 |

One-tenth of a gram of 3-chloro-2-(4-chloro-2-fluorophenyl)-4,5,6,7-tetrahydro-2H-indazole is dissolved in 9.9 grams of dimethylformamide. This solution is very slowly atomized onto 190.1 grams of rapidly tumbling bed of the attapulgite granules. After application of the active is complete, the formulation is blended for a few additional minutes. The dimethylformamide is not removed from the formulation. The granules are packaged for use.

EXAMPLE 20

| Emulsifiable Concentrate | |
|---|---|
| 3-chloro-2-(4-chloro-2-fluorophenyl)-4,5,6,7-tetrahydro-2H-indazole | 20% |
| blend of oil-soluble sulfonate with polyoxyethylene ethers | 6% |
| aromatic hydrocarbon solvent with a Tag closed cup flash point between 100 and 115° F. | 74% |

-continued

The ingredients are combined and stirred until solution is complete. The solution is filtered through a fine screen filter prior to packaging to remove any extraneous undissolved material.

EXAMPLE 21

| Low Strength Granules | |
|---|---|
| 3-chloro-2-(4-chloro-2-fluorophenyl)-4,5,6,7-tetrahydro-2H-indazole | 0.1% |
| sodium ligninsulfonate | 5% |
| preformed sand granules having a particle size distribution from USS sieve No. 140 (105 microns) to USS Sieve No. 50 (297 microns) | 94.9% |

0.5 gm. 3-chloro-2-(4-chloro-2-fluorophenyl)-4,5,6,7-tetrahydro-2H-indazole and 25 gm sodium ligninsulfonate are dissolved in 50 gm water. This solution is slowly sprayed onto a tumbling bed of the sand granules (474.5 gms.). After spraying is complete the tumbling granules are warmed to remove the water. The resulting granules are packaged for use.

Compositions can contain, in addition to the active ingredients of this invention, other conventional agricultural chemicals such as fertilizers, plant growth modifiers or herbicides.

For example, the compounds of Formula I can be combined with the following herbicides:

1. 5-tert-butyl-3-(2,4-dichloro-5-isopropoxyphenyl)-1,3,4-oxadiazol-2one;
2. 6-methylthio-2,4-bis(ethylamino)-s-triazine;
3. 3-isopropyl-(1H)-benzo-2,1,3-thiodiazin-4-one-2,2-dioxide;
4. 2,4-dichlorophenoxyacetic acid and related esters and salts. Combinations with wheat herbicides:

1. 2,4-dichlorophenoxyacetic acid and related esters and salts:
2. S-(2,2,3-trichloroallyl)-diisopropylthiocarbamate;
3. Methyl 2-[4-(2,4-dichlorophenoxy(phenoxy)]-propanoate;
4. 1,2-dimethyl-3,5-diphenyl-1H-pyrazolium methyl sulfate;
5. 4-chloro-2-butynyl 3-chlorocarbanilate.

The compounds of Formula I can also be combined with other herbicides and are particularly useful in combination with bromacil [3-(sec-butyl)-5-bromo-6-methyluracil], diuron [3-(3,4-dichlorophenyl)-1,1-dimethylurea], 3-cyclohexyl1-methyl-6-dimethylamino-s-triazine-2,4(1H,3H)-dione, paraquat [1,1'-dimethyl-4,4'-bipyridinum ion], m-(3,3-dimethylureido) phenyl tert-butylcarbamate, 2-methyl-4-chlorophenoxyacetic acid, its salts or esters, 4-amino-6-tert-butyl-3-methylthioas-triazin-5(4H)-one, aryl 4-nitrophenyl ethers such as 2,4,6-trichlorophenyl 4-nitrophenyl ether and 2,4-dichlorophenyl 4-nitrophenyl ether for controlling a broad spectrum of weeds.

The agricultural chemicals listed above are exemplary of the compounds which can be mixed with the active compounds and are not intended to limit the invention in any way.

EXAMPLE 24

For industrial use, a granule may be made from

| | |
|---|---|
| 3-chloro-2-(4-chlorophenyl)-4,5,6,7-tetrahydro-2H-indazole | 5% |
| 3-cyclohexyl-1-methyl-6-dimethylamino-s-triazine-2,4(1H,3H)-dione | 5% |
| #25-50 attapulgite granules (low volatile matter, 0.71 mm.-0.30 mm. diameter) | 90% |

The active ingredients are mixed and then warmed to approximately 90° and sprayed onto the dedusted and prewarmed granules in a double cone blender. The treated granules are then allowed to cool and are packaged.

UTILITY

The compounds of Formula I are useful for the selective preemergence control of undeired vegetation, e.g., barnyardgrass, in crops such as rice, in particular paddy rice, wheat, and peanuts. These compounds also have utility for the postemergence control of weeds in certain crops, for example, rice. Furthermore, compounds of this invention can be used as directed treatments for the pre- or post-emergence control of weeds in various crops including soybeans, peanuts, cotton, garden beans and rowplanted rice.

The componds of this invention are useful for the control of weeds in transplanted crops such as rice, tobacco, tomatoes, cabbage, sweet potatoes, lettuce, celery, peppers, and eggplant. The treatment may be applied to the soil surface prior to transplanting and the crop transplanted through the treated soil or it may be soil incorporated prior to transplanting and the crop set in the treated soil. It may also be applied after the crop is transplanted if care is taken to keep the chemical off the crop foliage (Table IV).

The precise amount of the compounds of Formula I to be used in any given situation will vary according to the particular end result desired, the use involved, the crop and weed species, and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.015 to about 15 kilograms per hectare, preferably about 0.03 to about 10 kilograms per hectare. The lower rates in this range will generally be selected on lighter soils, soils low in organic matter content, for selective weed control in crops, or in situations where maximum persistance is not necessary.

Herbicidal activity of compounds of this invention was discovered in greenhouse tests, as explained below:

PROCEDURE TEST 1

Seeds of crabgrass (*Digitaria spp.*), barnyardgrass (*Echinochloa crusgalli*), wild oats (*Avena fatua*), *Cassia tora*, morningglory (*Ipomoea sp.*), cocklebur (*Xanthium sp.*), sorghum, corn, soybean, rice, wheat and nutsedge tubers were planted in a growth medium and treated preemergence with the chemicals dissolved in a nonphytotoxic solvent. At the same time, cotton having five leaves (including, cotylendonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment.

Ratings for compounds tested by this procedure are recorded in Table 1. Plant response was expressed on a scale extending from 0 = no injury to 10 = complete kill. Letter symbols used had the following meamings: B = burn, G = growth retardation, C = necrosis/chlorosis, E = emergence inhibition, and H = formative effect: X = axillary stimulation.

TABLE 1
| COMPOUND | KG PER HEC-TARE | BUSH BEAN | COT-TON. | SOR-GHUM | CORN | SOY-BEAN | WHEAT | WILD OATS | RICE | BARN-YARD-GRASS | CRAB-GRASS | MORNING-GLORY | COCKLE-BUR | CAS-SIA | NUT-SEDGE |
|---|---|---|---|---|---|---|---|---|---|---|---|---|---|---|---|
| | POSTEMERGENCE | | | | | | | | | | | | | | |
| 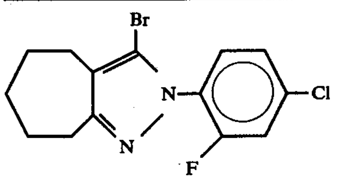 | 2/5 | 9B | 9B | 7B | 5B | 5B | 6B | 5B | 7B | 9B | 5B | 9B | 7B | 7B | 3B |
| 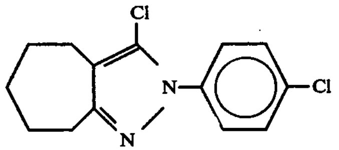 | 2 | 9B | 7B | 3B | 5B | 6B | 3B | 5B | 6B | 10B | 2B | 7B | 4B | 3B | 2B |
| 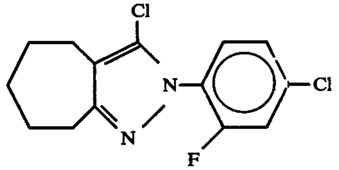 | 2/5 | 8B | 8B | 5B | 6B | 7B | 3B | 4B | 4B | 7B | 3B | 10B | 7B | 5B | 2B |
| 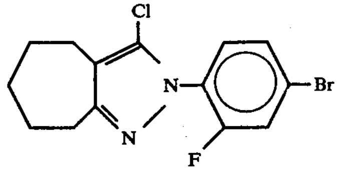 | 2/5 | 10B | 9B | 5B | 6B | 6B | 4B | 4B | 4B | 10B | 4B | 9B | 9B | 8B | 2B |
| 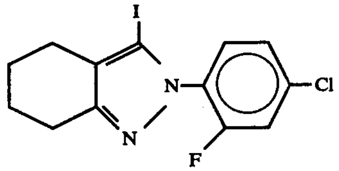 | 2/5 | 10B | 9B | 5B | 6B | 5B | 2B | 2B | 2B | 10B | 6B | 7B | 7B | 3B | 2B |
| 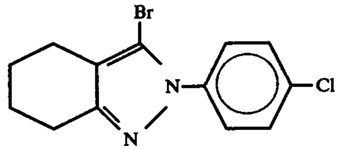 | 2/5 | 9B | 9B | 4B | 7B | 5B | 2B | 2B | 4B | 9B | 7B | 10B | 4B | 3B | 2B |

TABLE 1-continued
| | | | | | | | | | | | | | | | |
|---|---|---|---|---|---|---|---|---|---|---|---|---|---|---|---|
| 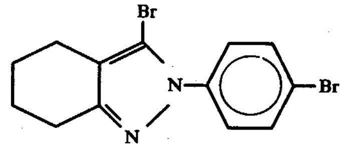 | 2 | 10B | 9B | 9B | 9B | 9B<br>5X | 8B | 8B | 10B | 10B | 9B | 10B | 6B | 6B | 4B |
| 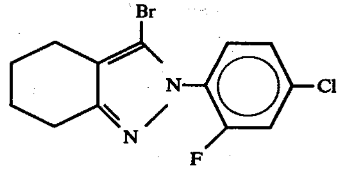 | 2 | 10B | 10B | 10B | 9B | 9B | 8B | 9B | 9B | 10B | 10B | 10B | 10B | 9B | 5B |
| 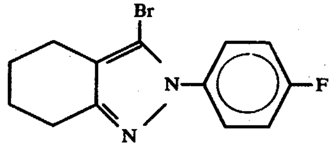 | 2 | 9B | 9B | 6B | 6B | 6B | 3B | 4B | 1B | 9B | 2B | B | 6B | 2B | 1B |
| 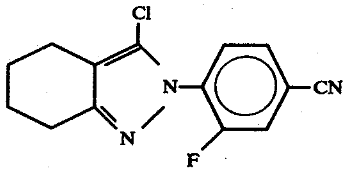 | 2<br>2/5 | 10B<br>10B | 10B<br>9B | 8B<br>10B | 10B<br>10B | 10B<br>9B | 10B<br>8B | 10B<br>9B | 10B<br>9B | 10B<br>10B | 10B<br>9B | 10B<br>10B | 10B<br>10B | 10B<br>9B | 8B<br>4B |
| 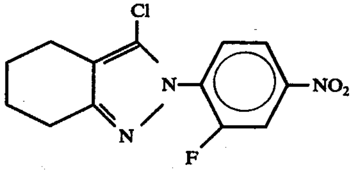 | 2/5 | 8B | 8B | 2B | 7B | 4B | 2B | 2B | 2B | 6B | 8B | 10B | 6B | 3B | 2B |
| 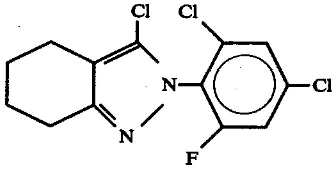 | 2 | 10B | 9B | 3B | 7B | 6B | 2B | 5B | 2B | 10B | 5B | 10B | 5B | 2B | 2B |
| 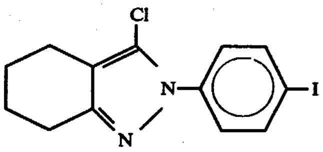 | 2/5 | 9B | 10B | 6B | 8B | 5B | 3B | 3B | 5B | 9B | 7B | 10B | 5B | 3B | 2B |

TABLE 1-continued
| | | | | | | | | | | | | | | | |
|---|---|---|---|---|---|---|---|---|---|---|---|---|---|---|---|
| 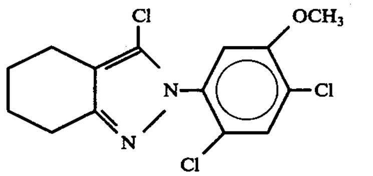 | 2 | 10B | 10B | 9B | 9B | 9B | 7B | 9B | 9B | 10B | 10B | 10B | 7B | 10B | 5B |
| 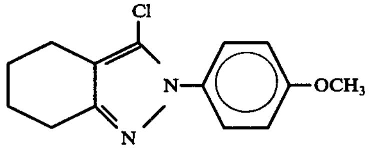 | 2 | 10B | 9G | 10B | 9B | 5B | 9B | 9B | 10B | 10B | 10B | 10B | 6B | 6B | 5B |
| 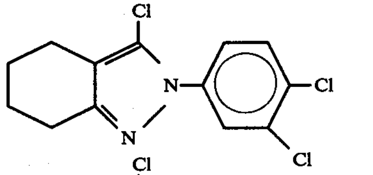 | 2 | 9B | 8B<br>7D | 6B | 6B | 6B | 6B | 6B | 6B | 10B | 3B<br>9H | 10B | 6B | 3B | 3B |
| 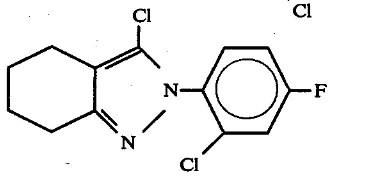 | 2 | 9B | 9B | 9B | 4B | 5B | 2B | 2B | 5B | 7B | 1B<br>5G | 9B | 5B | 2B | 1B |
| | 2/5 | 9B | 7B | 5B | 4B | 2B | 1B | 3B | 3B | 5B | 1B | 8B | 3B | 2B | 1B |
| 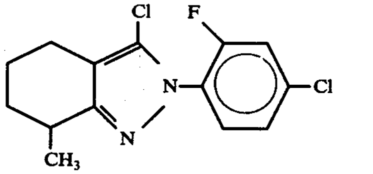 | 2<br>2/5 | 10B<br>9B | 9B<br>9B | 10B<br>6B | 9B<br>3B | 8B<br>3B | 8B<br>3B | 9B<br>6B | 9B<br>4B | 10B<br>10B | 10B<br>9B | 10B<br>10B | 7B<br>6B | 6B<br>4B | 3B<br>1B |
| 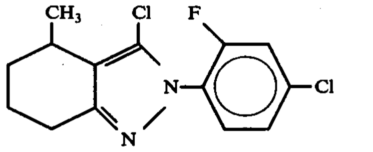<br>and<br>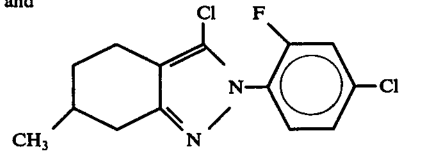 | 2<br>2/5 | 10B<br>10B | 10B<br>9B | 10B<br>9B | 10B<br>9B | 9B<br>8B | 9B<br>6B | 9B<br>9B | 9B<br>9B | 10B<br>10B | 10B<br>5B<br>8H | 10B<br>5B | 9B<br>10B | 10B<br>6B | 5B<br>5B |

TABLE 1-continued
| | | | | | | | | | | | | | | | |
|---|---|---|---|---|---|---|---|---|---|---|---|---|---|---|---|
| 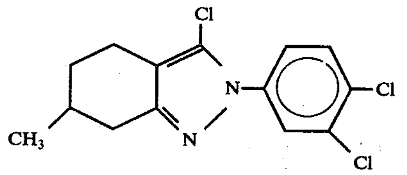 | 2 | 9B | 8B | 5B | 5B | 3B | 4B | 6B | 5B | 8B | 3B | 9B | 2B | 1B | 1B |
| 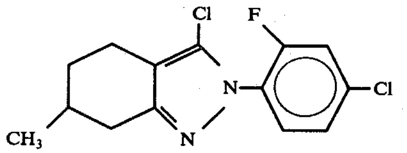 | 2/5 | 9B | 7B | 2B | 3B | 3B | 2B | 2B | 3B | 5B | 2B | 9B | 4B | 2B | 1G |
| 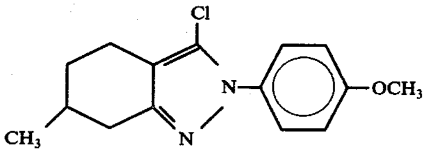 | 2/5 | 7B | 7B | 3B | 2B | 1B | 2B | 2B | 3B | 7B | 2B | 8B | 3B | 3B | 0 |
| 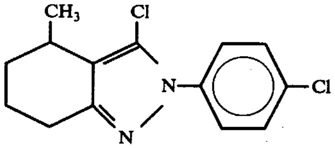 | 2 | 10B | 9B | 10B | 3B 5H | 8B 5X | 7B | 8B | 8B | 10B | 3B | 10B | 5B | 6B | 2B |
| and | | | | | | | | | | | | | | | |
| 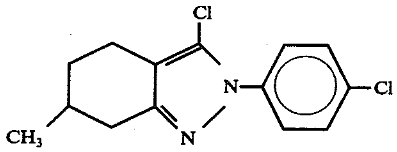 | 2/5 | 9B | 8B | 9B | 6B | 4B | 6B | 6B | 5B | 8B | 2B | 10B | 4B | 2B | 1B |
| 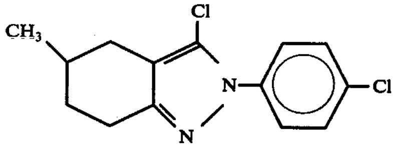 | 2/5 | 9B | 10B | 2B | 2B | 3B | 1B | 1B | 3B | 8B | 1B | 9B | 4B | 5B | 1B |

TABLE 1-continued
| | | | | | | | | | | | | | | | |
|---|---|---|---|---|---|---|---|---|---|---|---|---|---|---|---|
| 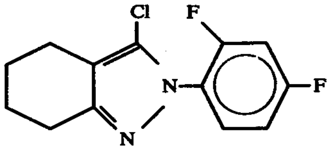 | 2/5 | 9B | 8B | 7B | 6B | 7B | 4B | 3B | 4B | 7B | 7B | 9B | 5B | 3B | 1B |
| 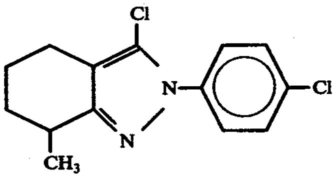 | 2 | 7B | 9B<br>9D | 4B | 5B | 10B | 2B | 2B | — | 9B | 4B<br>6H | 10B | 4B | 3B | 3B |
| | 2/5 | 8B | 7B<br>5D | 2B | 6B | 4B | 2B | 1B | 2B | 6B | 1B | 10B | 2B | 10B | 1B |
| 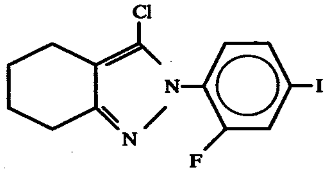 | 2/5 | 10B | 9B | 8B | 4B<br>9H | 8B | 2B | 5B | 9B | 10B | 4B | 10B | 6B | 3B | 2B |
| 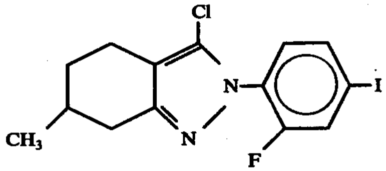 | 2/5 | 10B | 8B | 2G | 2C<br>6H | 2G | 2H<br>5C | 9C | 3C | 9C | 6B<br>1C | 10B | 6B | 6B | 3B |
| 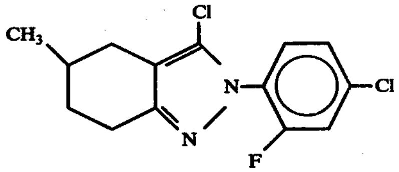 | 2/5 | 9B | 10B | 9B | 5B | 6B | 2B | 2B | 8B | 9B | 5B<br>9H | 10B | 7B | 9B | 2B |
| 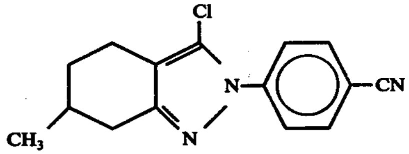 | 2/5 | 7B | 9B | 3B | 4B | 4B | 2B | 2B | 6B | 9B | 1B<br>5G | 10B | 2B | 1B | 1B |
| 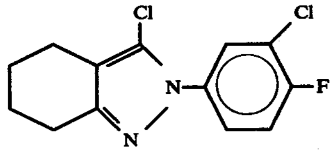 | 2/5 | 9B | 7B | 5B | 6B | 5B | 2B | 2B | 6B | 8B | 6B | 10B | 3B | 2B | 0 |

TABLE 1-continued
| | | | | | | | | | | | | | | | | |
|---|---|---|---|---|---|---|---|---|---|---|---|---|---|---|---|---|
| 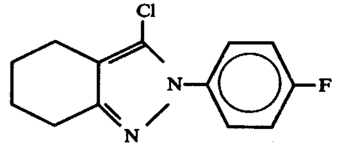 | 2/5 | 8B | 9B | 6B | 4B | 5B | 2B | 2B | 4B | 9B | 10B | 10B | 4B | 1B | 1B |
| 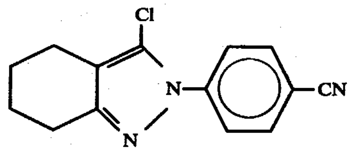 | 2/5 | 10B | 10B | 7B | 7B | 8B | 6B | 7B | 9C | 10B | 9B | 6B | 7B | 5B | 5B |
| 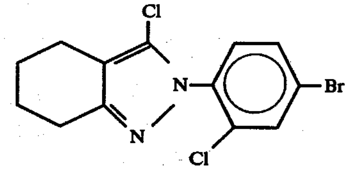 | 2<br>2/5 | 9B<br>9B | 10B<br>9B | 10B<br>8B | 7B<br>3B | 7B<br>5B<br>5X | 5B<br>2B | 7B<br>4B | 9B<br>7B | 10B<br>9B | 10B<br>10B | 10B<br>9B | 5B<br>5B | 8B<br>8B | 2B<br>1B |
| 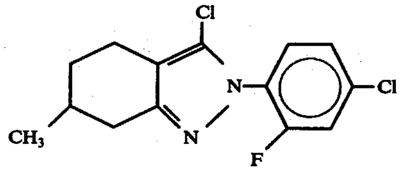 | 2/5 | 10B | 9B | 5B | 5B<br>9H | 9B | 6B | 8B | 5B | 9B | 8B | 10B | 9B | 6B | 3B |
| 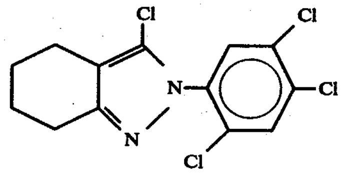 | 2/5 | 9B | 8B | 5B | 6B | 4B | 1B | 2B | 5B | 9B | 7B | 6B | 4B | 2B | 1B |
| 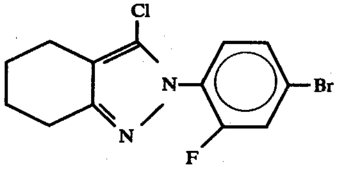 | 2<br>2/5 | 10B<br>10B | 10B<br>9B | 9B<br>9B | 9B<br>9B | 9B<br>8B<br>5X | 8B<br>6B | 10B<br>9B | 10B<br>9B | 10B<br>10B | 10B<br>9B | 10B<br>10B | 10B<br>10B | 10B<br>9B | 5B<br>2B |
| 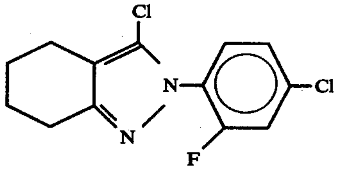 | 2 | 10B | 10B | 10B | 10B | 9B | 9B | 10B | 9B | 10B | 10B | 10B | 10B | 6B | 5B |

TABLE 1-continued
| | | | | | | | | | | | | | | | |
|---|---|---|---|---|---|---|---|---|---|---|---|---|---|---|---|
| 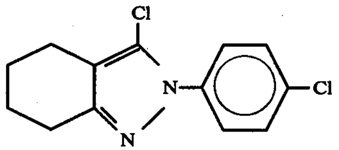 | 2 | 9B | 9B | 10B | 9B | 8B | 8B | 10B | 9G | 10B | 9B | 10B | 7B | 6B | 4B |
| 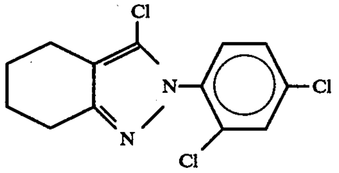 | 2 | 9C | 8B | 9B | 8B | 7B | 3B | 4B | 5B | 10B | 8B | 10B | 4B | 3C | 1B |
| 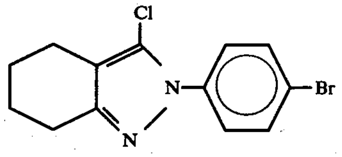 | 2 | 10B | 8B | 7B | 10B | 7B | 7B | 8B | 10B | 10B | 9B | 10B | 6B | 2B | 3B |
| 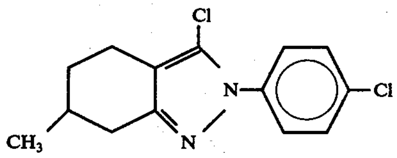 | 2 | 10B | 10B | 10B | 10B | 9B | 8B | 8B | 8B | 10B | 8B | 10B | 7B | 7B | 6B |
| 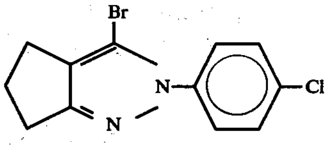 | 2/5 | 8B | 10B | 5B | 4B | 3B | 2B | 2B | 3B | 8B | 7B | 8B | 2B | 2B | 1B |
| 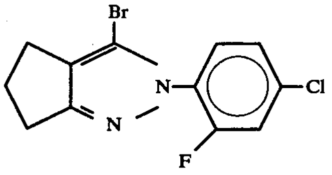 | 2/5 | 10B | 9B | 7B | 6B | 6B | 2B | 2B | 7B | 9B | 9B | 10B | 6B | 2B | 2B |
| 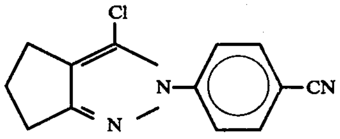 | 2<br>2/5 | 9B<br>9B | 9B<br>9B | 9B<br>7B | 7B<br>6B | 9B<br>8B | 4B<br>2B | 10B<br>7B | 9B<br>8B | 10B<br>9B | 9B<br>5B | 9B<br>9B | 10B<br>7B | 10B<br>2B | 4B<br>2B |

TABLE 1-continued
| | | | | | | | | | | | | | | | |
|---|---|---|---|---|---|---|---|---|---|---|---|---|---|---|---|
| 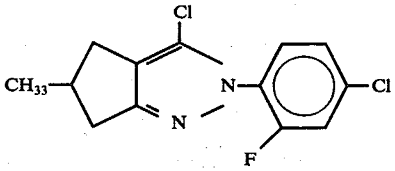 + 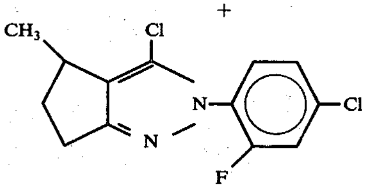 | 2/5 | 9B | 9B | 8B | 6B | 9B<br>5X | 3B | 7B | 7B | 9B | 6B | 9B | 5B | 5B | 3B |
| 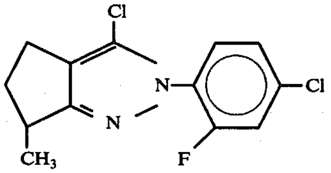 | 2/5 | 3B | 6B | 3B | 2B | 5B | 2B | 2B | 3B | 7B | 5B | 2B | 2B | 1B | 1B |
| 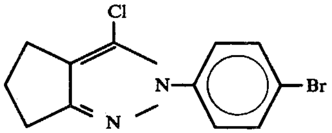 | 2 | 10B | 10B | 9B | 9B | 9B | 6B | 9B | 8B | 10B | 10B | 10B | 5B | 7B | 3B |
| 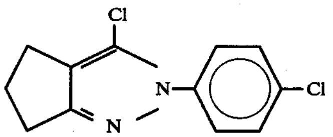 | 2/5 | 9B | 8B<br>8D | 7B | 2H<br>7B | 6B | 4B | 4B | 6B | 8B | 1B<br>9H | 9B | 5B | 2B | 2B |
| 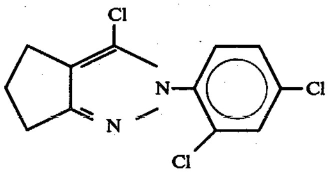 | 2/5 | 8B | 9B | 5B | 5B | 10B | 3B | 3B | 5B | 7B | 1B<br>5G | 10B | 5B | 6B | 1B |
| 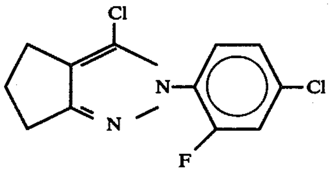 | 2/5 | 9B | 9B | 10B | 8B | 8B | 4B | 7B | 8B | 10B | 9B | 10B | 5B | 5B | 0 |

TABLE 1-continued
| | | | | | | | | | | | | | | | |
|---|---|---|---|---|---|---|---|---|---|---|---|---|---|---|---|
| 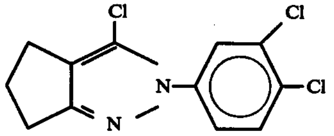 | 2/5 | 8B | 5B | 5B | 6B | 5B | 1B | 2B | 5B | 5B | 3B | 8B | 2B | 2B | 0 |
| 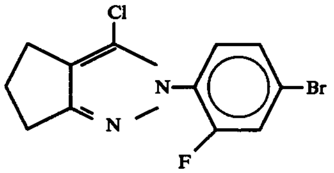 | 2 | 10B | 10B | 9B | 10B | 9B | 8B | 9B | 9B | 10B | 10B | 10B | 9B | 10B | 4B |
| 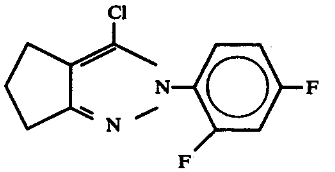 | 2<br>2/5 | 10B<br>3B | 10B<br>9B | 7B<br>2B | 5B<br>4B | 6B<br>5B | 1B<br>1B | 2B<br>1B | 4B<br>3B | 4B<br>3B | 4B<br>3B | 6B<br>4B | 3B<br>2B | 1B<br>1B | 1B<br>0 |
| 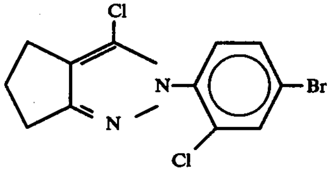 | 2<br>2/5 | 9B<br>5B | 9B<br>9B | 5B<br>4B | 3B<br>3B | 4B<br>3B | 1B<br>2B | 3B<br>1B | 5B<br>3B | 9B<br>7B | 2B<br>6H<br>3B | 10B<br>9B | 3B<br>2B | 7B<br>5B | 1B<br>1B |
| 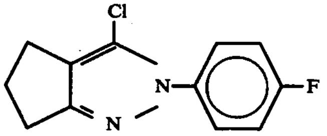 | 2<br>2/5 | 8B<br>4B | 8B<br>5B | 7B<br>4B | 6B<br>3B | 8B<br>— | 5B<br>2B | 6B<br>3B | 7B<br>3B | 8B<br>2B | 7B<br>2B | 5B<br>2B | 2B<br>1B | 1B<br>1B | 1B<br>1B |
| 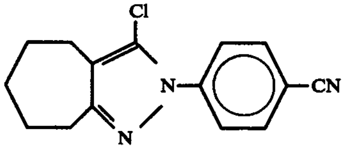 | 5 | 8B | 8B | 3B | 5B | 6B | 1B | 1B | 4B | 5B | 2B | 1B | 3B | 3B | 1B |
| 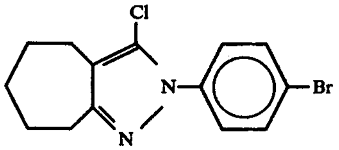 | 5 | 9B | 8B | 3B | 9B | 6B | 3B | 5B | 8B | 9B | 5B | 9B | 5B | 1B | 2B |

TABLE 1-continued
| | | | | | | | | | | | | | | |
|---|---|---|---|---|---|---|---|---|---|---|---|---|---|---|
| 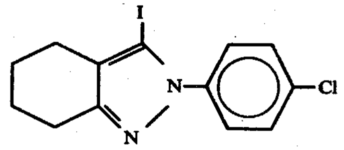 | 5 | 8B | 6B | 6B | 3B 6H | 5B | 2B | 3B | 2B | 9B | 4B | 6B | 5B | 1B | 1B |
| 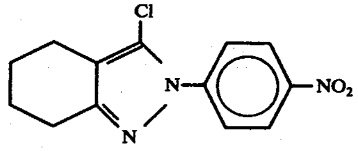 | 5 | 7B | 8B | 3B | 2B 6G | 5B | 1B | 1B | 2B | 9B | 5B | 9B | 4B | 3B | 1B |
| 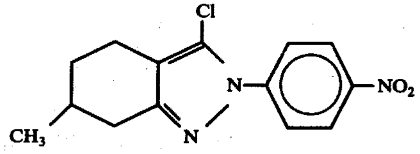 | 5 | 5B | 5B | 1B | 1B | 5B | 1B | 1B | 2B | 3B | 1B | 3B | 2B | 2B | 1B |
| 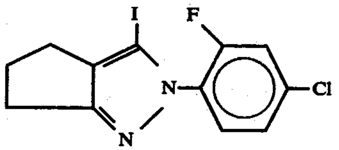 | 5 | 1B | 0 | 3B | 1B | 1B | 1B | 1B | 1B | 3B | 2B | 3B | 1B | 1B | 0 |
| 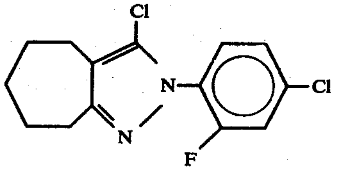 | 2/5 | 8B | 8B | 5B | 6B | 7B | 3B | 4B | 4B | 7B | 3B | 10B | 7B | 5B | 2B |
PREEMERGENCE
| COMPOUND | KG PER HEC-TARE | SORGHUM | CORN | SOYBEAN | WHEAT | WILD OATS | RICE | BARN-YARD-GRASS | CRAB-GRASS | MORNING-GLORY | COCKLE-BUR | CASSIA | NUT-SEDGE |
|---|---|---|---|---|---|---|---|---|---|---|---|---|---|
| 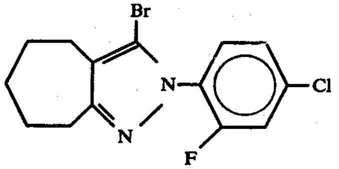 | 2/5 | 1C | 1C 7H | 1H | 4C | 2C | 5C | 2C 9H | 1H | 0 | 0 | 0 | 0 |

TABLE 1-continued
| | | | | | | | | | | | | | |
|---|---|---|---|---|---|---|---|---|---|---|---|---|---|
| 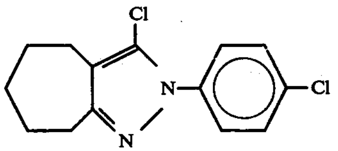 | 2 | 8L | 2C | 1H | 2C | 8C | 7C | 10C | 2H | 2G | 9C | 5G | 0 |
| 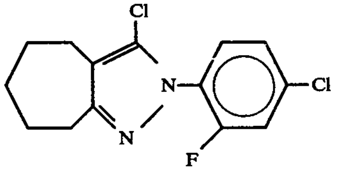 | 2/5 | 1C | 2C<br>8H | 6H | 2C | 3C | 2C<br>6G | 5C | 0 | 0 | — | 0 | 0 |
| 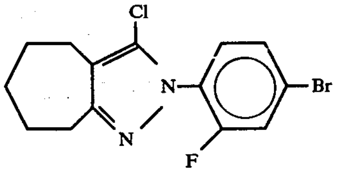 | 2/5 | 1C | 2C<br>3H | 1H | 5C | 5C | 1C | 10H | 8H | 0 | 9C | 0 | 0 |
| 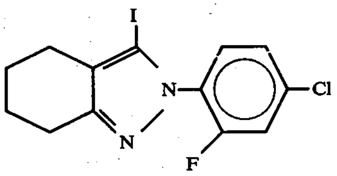 | 2/5 | 1C<br>5H | 2C<br>6H | 1C | 2C | 9C | 1C | 10C | 6H | 0 | 0 | 0 | 0 |
| 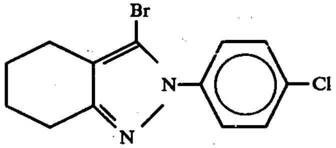 | 2/5 | 2C | 10H | 5G | 9C | 10C | 7C | 10C | 10E | 0 | 1H | 5H | 1C |
| 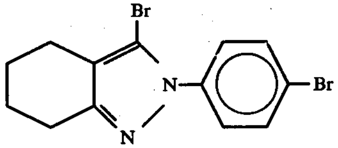 | 2 | 2C | 4C<br>9H | 1H<br>5G | 9C | 10C | 6C | 10C | 10C | 0 | 7G | 2C | 1C |
| 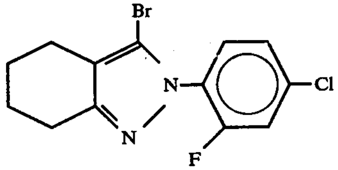 | 2 | 10C | 10C | 9H | 10C | 10C | 9C | 10E | 10E | 10C | 10C | 10C | 2C |

TABLE 1-continued
| | | | | | | | | | | | | | |
|---|---|---|---|---|---|---|---|---|---|---|---|---|---|
| 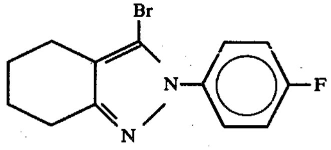 | 2 | 6C | 2C<br>6H | 2H | 5C | 6C | 8C | C | 2G | 2G | 0 | 2H | 0 |
| 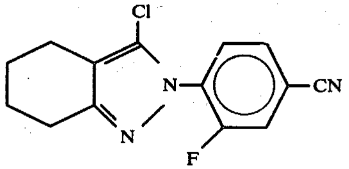 | 2<br>2/5 | 10C<br>10C | 10C<br>10C | 10C<br>10C | 9C<br>9C | 10C<br>10C | 10C<br>9C | 10C<br>10C | 10C<br>10C | 10C<br>10C | 10C<br>10C | 10<br>10 | 7C<br>7C |
| 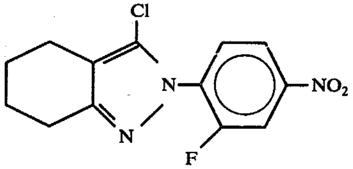 | 2/5 | 0 | 0 | 0 | 0 | 0 | 0 | 3H | 3G | 0 | 0 | 0 | 0 |
| 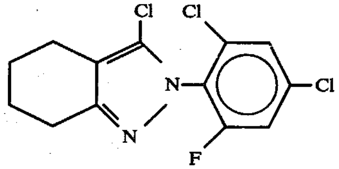 | 2 | 10E | 10H | 0 | 3C | 7C | 3C | 10E | 10E | 0 | 0 | 0 | 0 |
| 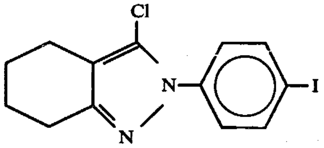 | 2/5 | 7G | 2C<br>8H | 1C | 7C | 7C | 5C | 9C | 5H | 0 | 3G | — | 0 |
| 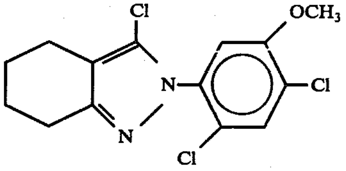 | 2 | 9C | 9H | 5G | 9C | 10C | 9C | 10C | 10H | 5G | 7G | 2C | 0 |
| 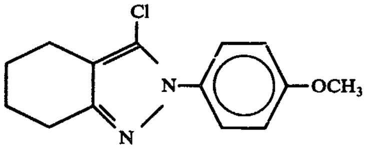 | 2 | 9C | 10H | 7H | 9C | 9C | 8C | 10C | 10C | 0 | 0 | 5G | 0 |

TABLE 1-continued
| | | | | | | | | | | | | | |
|---|---|---|---|---|---|---|---|---|---|---|---|---|---|
| 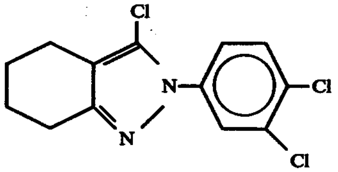 | 2 | 0 | 1C<br>6H | 2G | 7C | 7C | 5C | 8C | 10C | 0 | 10E | 0 | 0 |
| 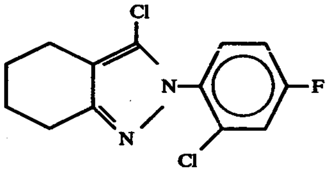 | 2<br><br>2/5 | 9C<br>1C<br>8H | 2C<br>7H<br>1C<br>2H | 1C<br><br>1H | 4C<br><br>1C | 8C<br><br>1C | 4C<br><br>2C | 9C<br>2C<br>7H | 5H<br><br>1C | 9C<br><br>0 | 0<br><br>— | 0<br><br>0 | 0<br><br>0 |
| 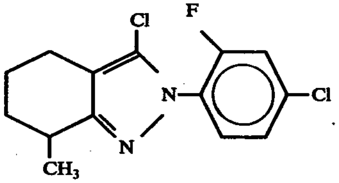 | 2<br>2/5 | 9C<br>9C | 10C<br>9C | 10C<br>9C | 9C<br>7C | 10C<br>9C | 8C<br>7C | 10C<br>10C | 9C<br>2G | 9C<br>10C | 0<br>0 | 0<br>0 | 1C<br>0 |
| 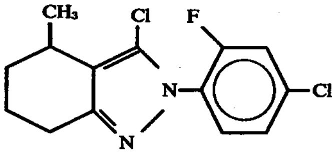<br>and<br>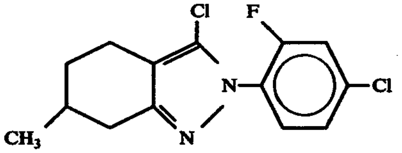 | 2<br>2/5 | 9H<br>1C<br>7G | 9C<br>3C<br>9H | 9H<br>9C | 9C<br>7C | 9C<br>9C | 9C<br>8C | 10C<br>10C | 10E<br>6C | 10C<br>10C | 9C<br>8G | 8C<br>2G | 2C<br>2C |
| 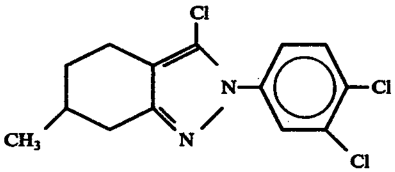 | 2 | 1C | 2C | 0 | 5C | 7C | 2C | 8C | 0 | 0 | 0 | 0 | 0 |

TABLE 1-continued
| | | | | | | | | | | | | | |
|---|---|---|---|---|---|---|---|---|---|---|---|---|---|
| 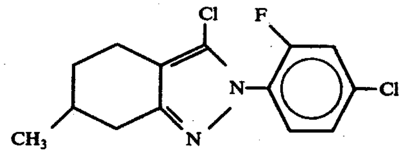 | 2/5 | 1C | 2C<br>6G | 2H | 6C | 7C | 2C | 9C | 2C | 2G | 0 | 0 | 0 |
| 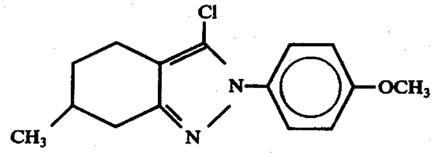 | 2/5 | 0 | 1C | 1H | 2C | 1C | 0 | 8C | 2C | 0 | 0 | 2C | 0 |
| 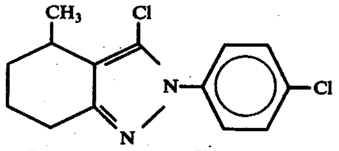<br>and<br>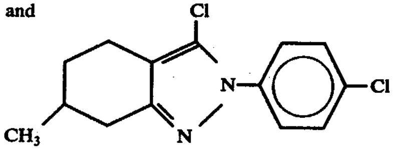 | 2 | 1C<br>7H | 9C | 7H | 5C | 5C | 8C | 9C | 1C | 56 | 0 | 0 | 0 |
| | 2/5 | 3C | 7C | 3G | 5C | 8C | 4C | 8C | 0 | 1H | 1H | 0 | 0 |
| 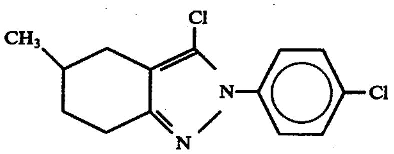 | 2/5 | 1C | 1C<br>7G | 4G | 4C | 7C | 3C | 1C<br>7H | 1C<br>6H | 0 | 0 | 0 | 0 |
| 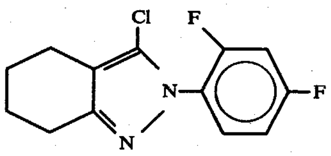 | 2/5 | 3C<br>8H | 2C<br>7G | 3H | 3C<br>7H | 9C | 6C | 10C | 1C<br>5G | 2H | 1H | 3G | 0 |
| 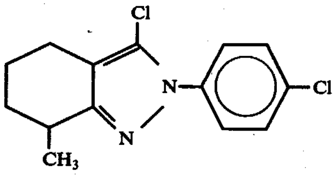 | 2 | 1C | 5C<br>8H | 3G | 7C | 9C | 9C | 10C | 1C<br>9H | 5G | 2H | 1C<br>3G | 0 |
| | 2/5 | 0 | 1C | 0 | 1C | 1C | 1C | 2C<br>9G | 3H | 0 | 0 | 0 | 0 |

TABLE 1-continued
| | | | | | | | | | | | | | |
|---|---|---|---|---|---|---|---|---|---|---|---|---|---|
| 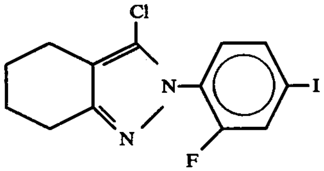 | 2/5 | 3C | 10H | 6H | 8C | 9C | 3C | 10C | 9C | 2G | 5G | 0 | 0 |
| 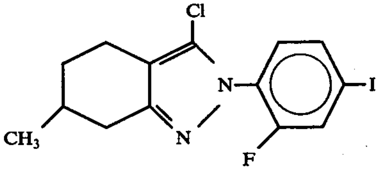 | 2/5 | 2G | 2C 6H | 2G | 2H 5C | 9C | 3C | 9C | 1C 5G | 10C | 0 | 0 | 0 |
| 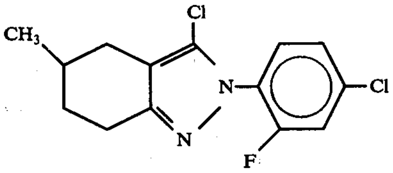 | 2/5 | 9C | 1C 9H | 3G | 1C 7G | 2C 8G | 2C 5G | 9C | 1C 6G | 8G | 5G | 5G | 0 |
| 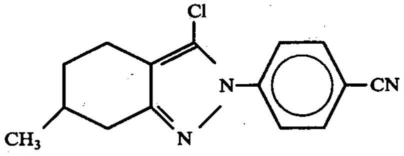 | 2/5 | 2C | 2C 9H | 0 | 2C 5G | 9C | 3C | 3C 8H | 5G | 5G | 0 | 1C | 0 |
| 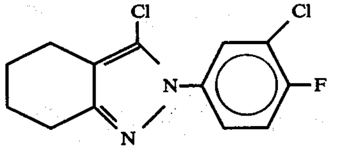 | 2/5 | 0 | 2H | 0 | 1C | 1C | 0 | 2G | 3G | 0 | 0 | 0 | 0 |
| 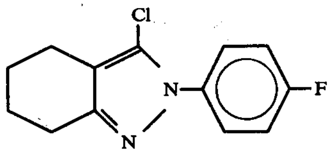 | 2/5 | 1C | 1C 5G | 1C 4G | 1C | 1C | 5C | 9C | 7G | 1H | 1H | 1H | 0 |
| 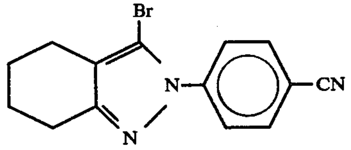 | 2/5 | 2G 1C | 9H | 9H | 8C | 10C | 9C | 10C | 2G | 0 | 4G | 6G | 6C |

TABLE 1-continued
| | | | | | | | | | | | | | |
|---|---|---|---|---|---|---|---|---|---|---|---|---|---|
| 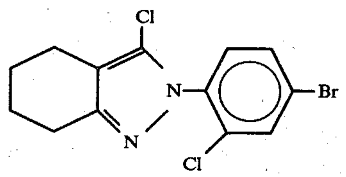 | 2<br>2/5 | 9C<br>9C | 2C<br>9H<br>1C<br>7H | 5H<br>0 | 3C<br>9H<br>2C<br>6H | 9C<br>2C<br>7H | 7C<br>2C | 10C<br>9C | 10C<br>1C<br>8H | 2G<br>0 | 2G<br>0 | 10E<br>0 | 0<br>0 |
| 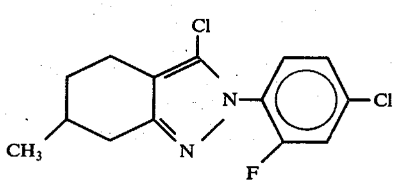 | 2/5 | 1C<br>6H | 2C<br>8H | 1C<br>2H | 5C | 6C | 5C | 8C | 5H | 1C<br>8H | 10E | 1C<br>5G | 0 |
| 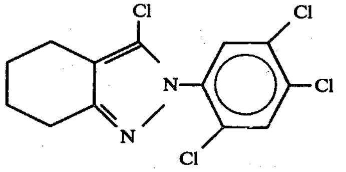 | 2/5 | 1C<br>6G | 2C<br>7H | 6H | 6C | 7C | 2C | 9C | 8H | 2G | 2G | 7G | 1C |
| 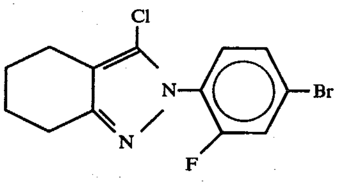 | 2<br>2/5 | 10C<br>10C | 10C<br>9C | 9C<br>1C<br>9H | 9C<br>9C | 10C<br>10C | 9C<br>8C | 10E<br>10E | 10E<br>10E | 5C<br>1X | 10E<br>10C | 10C<br>10C | 5C<br>1C |
| 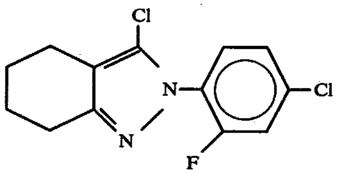 | 2 | 10C | 10C | 10C | 10C | 10C | 9C | 10C | 10C | 8G | 10C | 10C | 4C<br>6G |
| 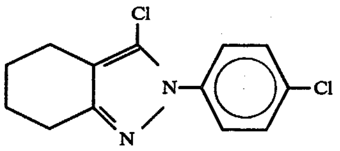 | 2 | 5C | 10C | 9H | 10C | 10C | 9C | 10E | 10E | 4G | 8C | 10C | 5C |

TABLE 1-continued
| | | | | | | | | | | | | | |
|---|---|---|---|---|---|---|---|---|---|---|---|---|---|
| 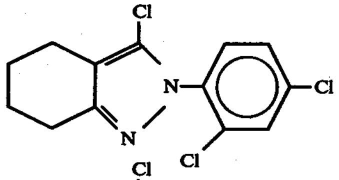 | 2 | 7C | 2C | 0 | 2C | 1C | 4C | 9C | 3C | 0 | 0 | 1C | 0 |
| 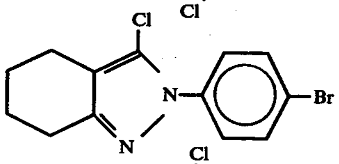 | 2 | 6C | 10C | 1C | 9C | 10C | 8C | 10C | 10C | 3G | 9C | 10C | 2C |
| 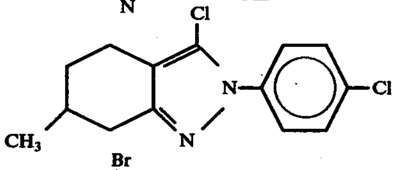 | 2 | 6C | 10C | 6G | 10C | 9C | 5C | 10C | 10C | 6G | 0 | 2C | 0 |
| 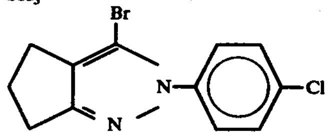 | 2/5 | 0 | 0 | 0 | 1C | 1C | 1C | 1C | 4G | 0 | — | 0 | 0 |
| 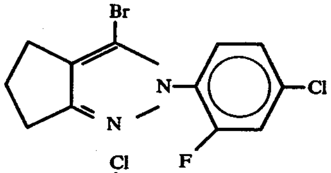 | 2/5 | 9C | 1C<br>8H | 8H | 1C<br>6H | 1C<br>7H | 7C | 10C | 10C | 0 | — | — | 0 |
| 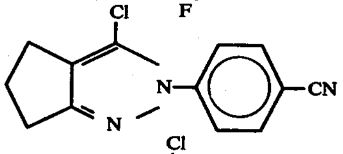 | 2<br>2/5 | 9C<br>1C<br>6G | 10C<br>2C<br>9H | 9C<br>5C | 9C<br>5C | 10C<br>9C | 9C<br>7C | 10C<br>10C | 1C<br>9H<br>1C<br>9H | 4G<br>2G | 0<br>0 | 1C<br>— | 3C<br>0 |
| 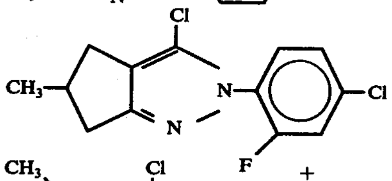 + 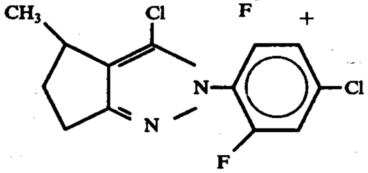 | 2/5 | 1C<br>7G | 2C<br>8G | 9H | 6C | 8C | 6C | 9C | 8G | 3G | 0 | 0 | 0 |

TABLE 1-continued
| | | | | | | | | | | | | | | |
|---|---|---|---|---|---|---|---|---|---|---|---|---|---|---|
| 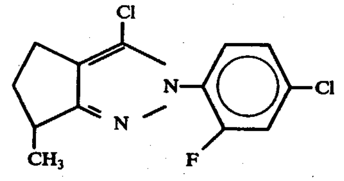 | 2/5 | 0 | 3G | 0 | 1H | 4G | 0 | 3H | 0 | 0 | 0 | 0 | 0 |
| 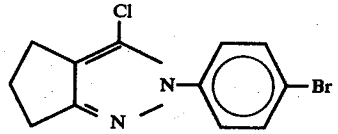 | 2 | 10C | 2C<br>9H | 6G | 9C | 10C | 8C | 10C | 10E | 1H | 0 | 5C | 1C |
| 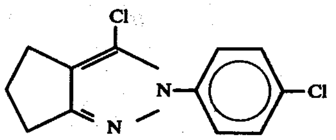 | 2/5 | 1C<br>5G | 1C<br>8H | 1H | 9C | 9C | 9C | 10C | 9H | 0 | 2G | 3G | 1C |
| 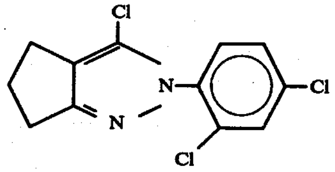 | 2/5 | 2C<br>6G | 3H | 1C | 1C<br>5G | 1C<br>6G | 5C | 9C | 6G | 0 | 0 | 0 | 0 |
| 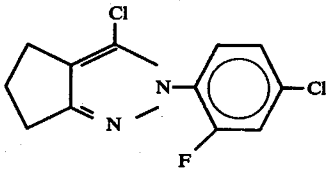 | 2/5 | 2C<br>9G | 1C<br>8G | 5H | 9H | 9H | 1C<br>5G | 10C | 10E | 3G | 3H | 5G | 0 |
| 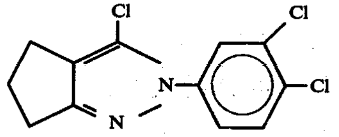 | 2/5 | 0 | 0 | 0 | 1C<br>4G | 1C<br>6G | 0 | 1C<br>6H | 10E | 0 | 0 | 0 | 0 |
| 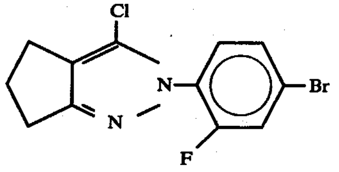 | 2 | 10C | 10C | 1C<br>8G | 10C | 10C | 9C | 10C | 10C | 3H | 1C<br>8G | 10C | 1C |

TABLE 1-continued
| | | | | | | | | | | | | | | |
|---|---|---|---|---|---|---|---|---|---|---|---|---|---|---|
| 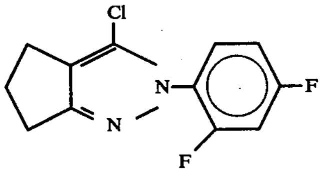 | 2 | 9C | 1C<br>7H | 2H | 2C<br>6H | 2C<br>8H | 1C<br>6G | 3C<br>9H | 3G | 2G | 0 | — | 0 |
| | 2/5 | 1C<br>5H | 1C | 0 | 1C<br>2H | 1C | 1C | 1C<br>5H | 2G | 0 | 0 | — | 0 |
| 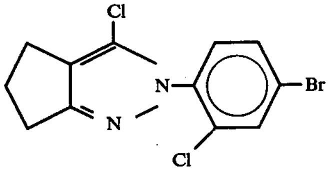 | 2 | 3C | 1C<br>5H | 5H | 5C | 1C<br>4H | 3C | 10C | 10C | 1C | 0 | 1C | 0 |
| | 2/5 | 3C | 1C<br>3G | 0 | 3C | 2C | 1C | 3C<br>9H | 9H | 0 | — | 0 | 0 |
| 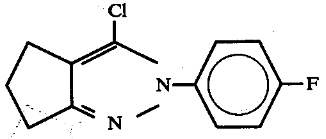 | 2 | 9C | 1C<br>3G | 2G | 4C | 9C | 4C | 8C | 1H | 1C | 0 | 10C | 0 |
| | 2/5 | 0 | 0 | 0 | 0 | 0 | 0 | 0 | 0 | 0 | 0 | 0 | 0 |
| 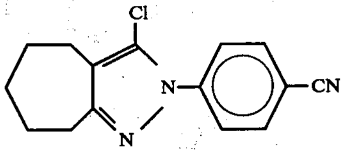 | 5 | 0 | 1C | 0 | 1C | 1C | 0 | 1C | 5G | 0 | 0 | 0 | 0 |
| 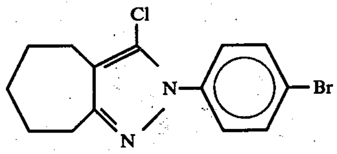 | 5 | 1C | 5H | 1H | 6C | 7C | 2C | 8C | 3G | 0 | 0 | 0 | 0 |
| 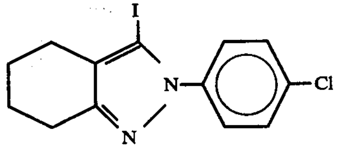 | 5 | 5C | 1C<br>5G | 0 | 5C | 8C | 3C | 9C | 5G | 0 | 0 | 0 | 0 |
| 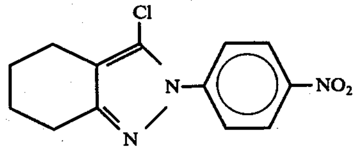 | 5 | 0 | 10H | 0 | 4H | 9C | 5C | 4C<br>8H | 8G | 0 | 0 | 0 | 0 |

TABLE 1-continued
| | | | | | | | | | | | | | |
|---|---|---|---|---|---|---|---|---|---|---|---|---|---|
| 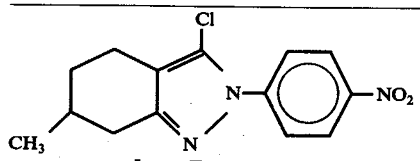 | 5 | 0 | 1C | 0 | 0 | 1C | 0 | 1C | 5G | 0 | 0 | 0 | 0 |
| 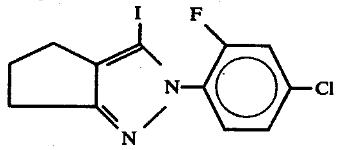 | 5 | 0 | 0 | 0 | 0 | 0 | 0 | 1C | 2G | 0 | — | 0 | 0 |
| 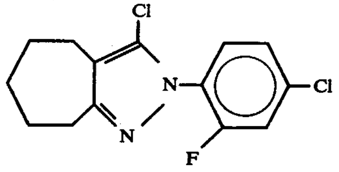 | 2/5 | 1C | 2C 8H | 6H | 2C | 3C | 2C 6G | 5C | 0 | 0 | — | 0 | 0 |

Table 2, is presented to further illustrate the bioligical activity of the compounds of this invention. The data illustrate the herbicidal efficacy of the compounds with selectivity for two important crops, rice and wheat.

The test compounds were applied in a non-phytotoxic solvent to soil pots containing seeds of an intermediate hybrid rice, japonica rice, barnyardgrass (*Echinochloa crusgalli*), morning glory (*Ipomoea sp.*), wheat, wild oats (*Avena fatua*), downy brome (*Bromus tectorum*), and cheat (*Bromus secalinus*). In addition, wild mustard (*Brassica arvenis*), Kochia (*Kochia scoparia*), and blackgrass (*Alopecurus myosuroides*) seeds were included in some instances, as were established plantings (postemergence) of some or all of the species mentioned above. The plants were maintained in a greenhouse (glasshouse), and visual plant response ratings (as described in Table 1) were generally taken about three weeks after application.

Table 2

| | | Preemergence | | | | | | | | | | |
|---|---|---|---|---|---|---|---|---|---|---|---|---|
| Compound | kg ai/ha | Intermediate Rice | Japonica Rice | Barnyardgrass | Morningglory | Wheat | Wild Oats | Bromus tectorum | Bromus secalinus | Wild Mustard | Kochia | Blackgrass |
| 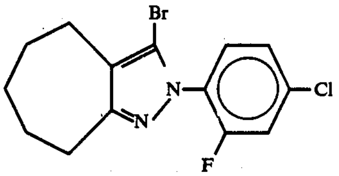 | 1/16 | 0 | 0 | 0 | 0 | 0 | 0 | 0 | 0 | | | |
| | 1/8 | 0 | 0 | 0 | 0 | 0 | 0 | 0 | 0 | | | |
| | 1/4 | 0 | 0 | 5C | 0 | 0 | 0 | 0 | 0 | | | |
| | 1/2 | 0 | 0 | 5C | 0 | 0 | 0 | 0 | 0 | | | |
| 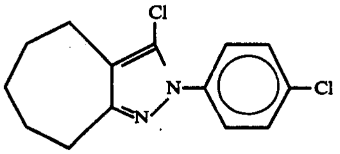 | 1/2 | 0 | — | 3C | 6G | | | | | | | |
| | 2 | 3C | 5C | 8C | 0 | | | | | | | |
| 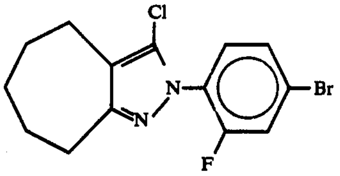 | 1/32 | 0 | 0 | 0 | 0 | 0 | 0 | 0 | 0 | | | |
| | 1/16 | 0 | 0 | 0 | 0 | 0 | 0 | 0 | 0 | | | |
| | 1/4 | 0 | 0 | 1C | 0 | 0 | — | 0 | 0 | | | |
| | 1/2 | 0 | 0 | 7C | 0 | 0 | 0 | 3G | 3C | | | |
| 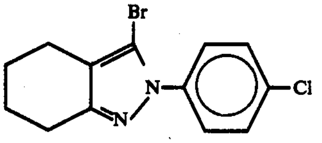 | 1/32 | 0 | 0 | 0 | 0 | 0 | 0 | 0 | 0 | | | |
| | 1/16 | 0 | 0 | 0 | 0 | 0 | 0 | 0 | 0 | | | |
| | 1/8 | 0 | — | — | 0 | 0 | 0 | 5G | 3G | | | |
| | 1/4 | 0 | 0 | 3G | 0 | — | — | — | — | | | |
| 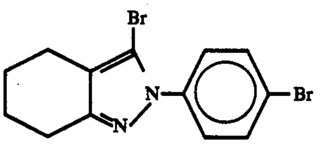 | 1/8 | 0 | 0 | 0 | 0 | 0 | 0 | 0 | 0 | | | |
| | 1/2 | 0 | 0 | 2C | 0 | 0 | 0 | 3G | 1G | | | |
| 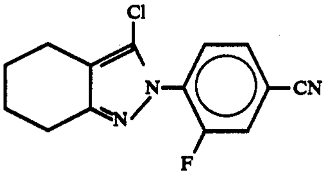 | 1/16 | 0 | 0 | 3G | 0 | 0 | 0 | 0 | 0 | | | |
| | 1/8 | 0 | 0 | 9G | 0 | 0 | 0 | 5G | 6G | | | |
| | 1/4 | 0 | 0 | &C | 0 | 1C | 8C | 9C | 8C | | | |
| | 1/2 | 0 | 0 | &C | 0 | 2C | &C | &C | 9C | | | |
| 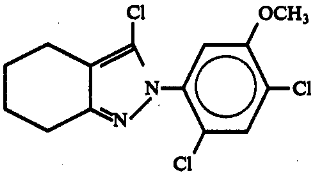 | 1/32 | 0 | 0 | 0 | 0 | 0 | 0 | 0 | 0 | | | |
| | 1/16 | 0 | 0 | 4C | 0 | 0 | 0 | 0 | 0 | | | |
| | 1/8 | — | — | 5C | — | 0 | 0 | 0 | 0 | | | |
| | 1/4 | — | 0 | 8C | 0 | 0 | 0 | 0 | 0 | | | |
| 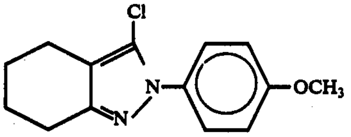 | 1/32 | 0 | 0 | 0 | 0 | 0 | 0 | 0 | 0 | 0 | 0 | — |
| | 1/8 | — | 0 | 0 | 0 | 0 | 0 | 0 | 0 | 0 | 0 | — |
| | 1/2 | 2G | 1G | 9C | 0 | 0 | 0 | 0 | 5G | 0 | 0 | — |

Table 2-continued
| | | | | | | | | | |
|---|---|---|---|---|---|---|---|---|---|
| 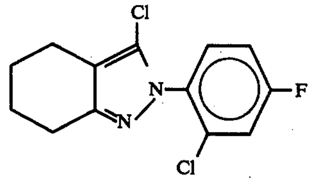 | 1/4 | 0 | 0 | 0 | 0 | 0 | 0 | 0 | 0 |
| | 1 | 0 | 0 | 3C | 0 | 1G | 1C | 3G | 0 |
| 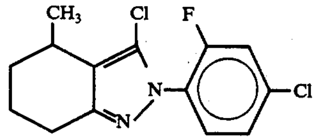 and | 1/8 | 0 | 0 | 0 | 0 | 0 | 0 | 0 | 0 |
| 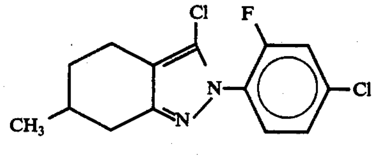 | 1/2 | — | 0 | 9C | 8G | 2C | 7C | 8C | 7C |
| 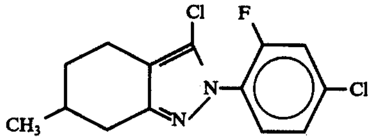 | 1/16 | 0 | 0 | 0 | 0 | 0 | 0 | 0 | 0 |
| | 1/8 | 0 | 0 | 0 | 0 | 0 | 0 | 0 | 0 |
| | 1/4 | 0 | 0 | 4G | 0 | 0 | 0 | 0 | 0 |
| | 1/2 | — | — | 9G | 0 | 1C | 1C | 4G | 4G |
| 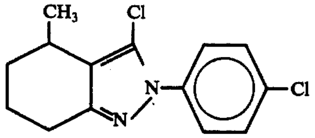 and | 1/4 | 0 | 0 | 0 | 0 | 0 | 0 | 0 | 0 |
| 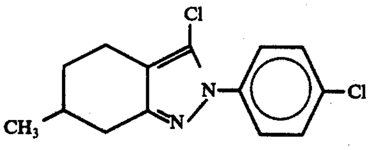 | 1 | — | 0 | 4C | 0 | 2C | 0 | 3G | 7C |
| 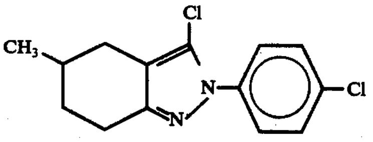 | 1/16 | 0 | 0 | 0 | 0 | 0 | 0 | 0 | 0 |
| | 1/8 | 0 | 0 | 0 | 0 | 0 | 0 | 0 | 0 |
| | 1/2 | 0 | 0 | 2G | 0 | 0 | 2G | 0 | 0 |
| 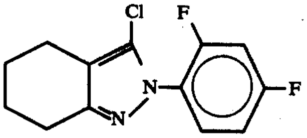 | 1/6 | 0 | 0 | 6G | 0 | 0 | 1C | 0 | 0 |
| | 1/8 | 0 | 0 | 7G | 0 | 1C | 3C | 0 | 0 |
| | 1/4 | 0 | 0 | 9G | 0 | 1C | 3C | 1C | 1C |
| | 1/2 | 0 | 0 | 10C | 0 | 3C | 3C | 5G | 5G |
| | | | | | | | | 1C | 2C |
| 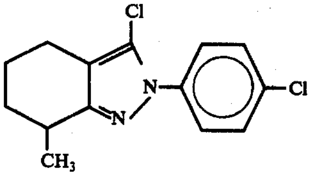 | 1/16 | 0 | 0 | 0 | 0 | 0 | 0 | 0 | 0 |
| | 1/8 | 0 | 0 | 0 | 0 | 0 | 0 | 0 | 0 |
| | 1/4 | 0 | 0 | 1G | 0 | 0 | 0 | 1G | 0 |
| | 1/2 | 0 | 0 | 3G | 0 | 0 | 3G | 4G | 1G |
| 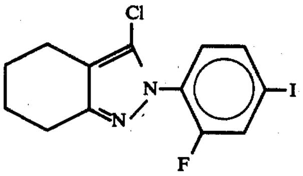 | 1/32 | 0 | 0 | 0 | 0 | 0 | 0 | 0 | 0 |
| | 1/16 | 0 | 0 | 0 | 0 | 0 | 0 | 0 | 0 |
| | 1/4 | 0 | 0 | 9C | 0 | 0 | 0 | 0 | 0 |
| | 1/2 | 0 | — | 10C | 0 | 1G | 4G | 7G | 5G |

Table 2-continued
| | | | | | | | | | | | | |
|---|---|---|---|---|---|---|---|---|---|---|---|---|
| 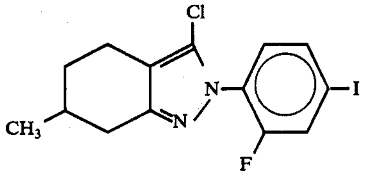 | 1/32 | 0 | 0 | 0 | 0 | 0 | 0 | 0 | 0 | | | |
| | 1/16 | 0 | 0 | 0 | 0 | 0 | 0 | 0 | 0 | | | |
| | 1/4 | 0 | 0 | 0 | 0 | 0 | 0 | 0 | 0 | | | |
| | 1/2 | 0 | 0 | 9C | 0 | 0 | 0 | 3G | 3G | | | |
| 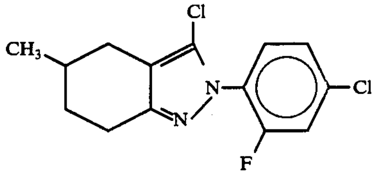 | 1/16 | 0 | 0 | 0 | 0 | 0 | 0 | 0 | 0 | | | |
| | 1/8 | 0 | 0 | 2G | 0 | 0 | 0 | 0 | 0 | | | |
| | 1/2 | 0 | 0 | 10C | 0 | 1C | 5C | 5C | 0 | | | |
| 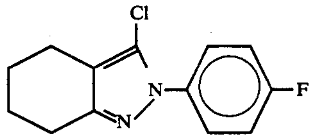 | 1/4 | 0 | 0 | 0 | 0 | 0 | 0 | 0 | 0 | | | |
| | 1/2 | 4C | 0 | 7C | 0 | 0 | 0 | 0 | 0 | | | |
| | 1 | 4C | 0 | 3C | 0 | 1C | 0 | 1C | 1C | | | |
| | 2 | 8C | 0 | 9C | 0 | 5C | 0 | 0 | 8C | | | |
| 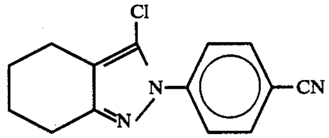 | 1/32 | 0 | 0 | 0 | 0 | 0 | 0 | 0 | 0 | | | |
| | 1/16 | 0 | 0 | 0 | 0 | 0 | 1C | 0 | 0 | | | |
| | 1/4 | 0 | 0 | 9C | 0 | — | 3C | 0 | — | | | |
| | 1/2 | 2G | 0 | 10C | 0 | 0 | 8C | 5C | 0 | | | |
| 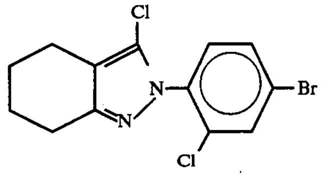 | 1/32 | 0 | 0 | 0 | 0 | 0 | 0 | 0 | 0 | | | |
| | 1/16 | 0 | 0 | 2C | 0 | 0 | 0 | 0 | 0 | | | |
| | 1/4 | 0 | 0 | 7C | 0 | 0 | 0 | 0 | 0 | | | |
| | 1/2 | 0 | 0 | 8C | 0 | 0 | 0 | 0 | 0 | | | |
| 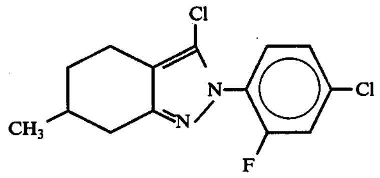 | 1/32 | — | 0 | 0 | 0 | 0 | 0 | 0 | 0 | 0 | 5C | — |
| | 1/16 | 0 | 0 | 2C | 0 | 0 | 0 | 2G | 0 | 0 | 6C | — |
| | 1/4 | 0 | 0 | 10C | 0 | 0 | 1G | 9C | 9C | 5C | 10C | — |
| | 1/2 | 1G | 0 | 10C | 2G | 0 | 8G | 10C | 10C | 10C | 10C | — |
| 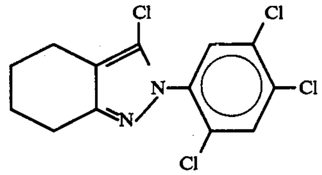 | 1/32 | 0 | — | 0 | 0 | 0 | 0 | 0 | 0 | — | — | — |
| | 1/16 | 0 | 0 | 3G | 0 | 0 | 0 | 0 | 0 | — | — | — |
| | 1/4 | 0 | 0 | 5G | 0 | 0 | 0 | 0 | 0 | — | — | — |
| | 1/2 | 0 | 0 | 7G | 0 | 0 | 2G | 0 | 0 | — | — | — |
| 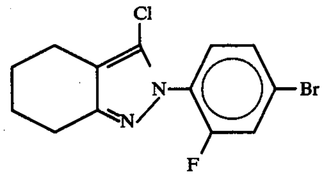 | 1/16 | 0 | 0 | 9C | 0 | 0 | 0 | 0 | 0 | — | — | — |
| | 1/8 | 0 | 0 | 9C | 0 | 1C | 2C | 5C | 2C | — | — | — |
| | 1/4 | 0 | 0 | 9C | 0 | 1C | 2C | 5C | 6C | — | — | — |
| | 1/2 | 1C | 0 | 10C | 1G | 3C | 8C | 9C | 9C | — | — | — |
| | 1 | 3C | 1C | 10C | 2G | 4C | 9C | 9C | 10C | — | — | — |
| 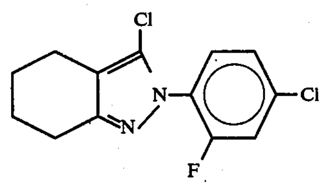 | 1/64 | 0 | 0 | 5G | 0 | 0 | 0 | 0 | 0 | 0 | 0 | 5E |
| | 1/32 | 0 | 0 | 9G | 0 | 0 | 1G | 3G | 3G | 0 | 3C | 5E |
| | 1/16 | 0 | 0 | 9G | 0 | 0 | 5G | 8G | 3G | 3G | 10C | 7E |
| | 1/8 | 0 | 0 | 10C | 2G | 0 | 6G | 10C | 4G | 6G | 10C | 9E |
| | 1/4 | 0 | 0 | 10C | 4G | 2G | 9C | 10C | 9C | 9C | 10C | 9G |
| | | | | | | | | | | | | 9E |
| | | | | | | | | | | | | 9G |
| 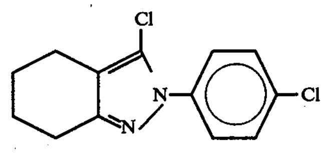 | 1/4 | 0 | 0 | 7C | 0 | 0 | 0 | 0 | 0 | — | — | 0 |
| | 1/2 | 0 | 0 | 8C | 0 | 0 | 3G | 0 | 7C | — | — | 6C |
| | 3/4 | 0 | 0 | 10C | 0 | 0 | 2G | 9C | 8C | — | — | 8C |
| | 1 | 0 | 0 | 10C | — | 1G | 9C | 10C | 10C | — | — | 8C |
| | 2 | 6C | 0 | 10C | 0 | 2C | 10C | 10C | 10C | — | — | 10C |

Table 2-continued
| | | | | | | | | | | | | |
|---|---|---|---|---|---|---|---|---|---|---|---|---|
| 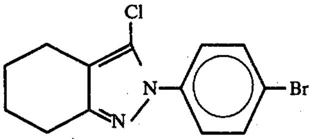 | 1/16 | 0 | 0 | 0 | 0 | 0 | 0 | 0 | 0 | 10C | 0 | — |
| | 1/8 | 0 | 0 | 3G | 0 | 0 | 0 | 0 | 0 | 10C | 3C | — |
| | 1/4 | 0 | 0 | 7G | 0 | 0 | 3G | 0 | 0 | 10C | 4C | — |
| | 1/2 | 0 | 0 | 9C | 0 | 0 | 1C 2G | 4G | 6G | 10C | 9C | — |
| 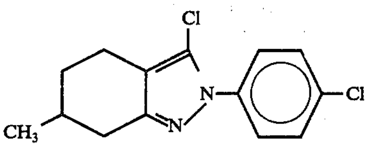 | 1/8 | 0 | 0 | 0 | 0 | 0 | 0 | 0 | 0 | 0 | 0 | — |
| | 1/2 | 0 | 0 | 3C | 0 | 0 | 2G | 0 | 0 | 0 | 5C | — |
| 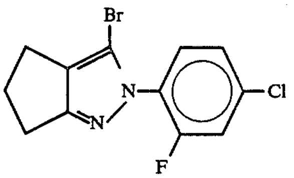 | 1/32 | 0 | 0 | 0 | 0 | 0 | 0 | 0 | 0 | | | |
| | 1/16 | 0 | 0 | 3C | 0 | 0 | 0 | 0 | 0 | | | |
| | 1/8 | 0 | 0 | 9C | 0 | 0 | 0 | 0 | 0 | | | |
| | 1/4 | 0 | 0 | 10C | 3G | 0 | 3C | 3C | 0 | | | |
| 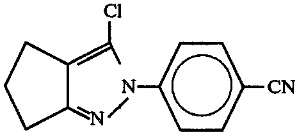 | 1/16 | 0 | 0 | 0 | 0 | 0 | 0 | 0 | 0 | | | |
| | 1/8 | 0 | — | 0 | 0 | 0 | 0 | 0 | 0 | | | |
| | 1/4 | 0 | — | 3G | 0 | 0 | 0 | 3G | 2G | | | |
| | 1/2 | 0 | 0 | 9G | 0 | 0 | 1C | 3G | 3G | | | |
| 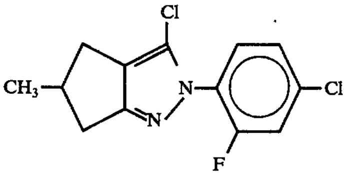 and 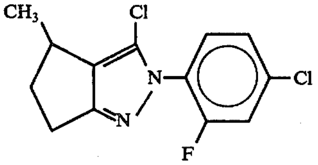 | 1/16 | 0 | 0 | 1G | 0 | 0 | 0 | 0 | 0 | | | |
| | 1/8 | 0 | 0 | 5G | 0 | 0 | 0 | 1G | 0 | | | |
| | 1/4 | 0 | 0 | 9C | 0 | 0 | 2C | 5C | 0 | | | |
| | 1/2 | 1C | 0 | 9C | 10C | 0 | 4G | 9C | 5G | | | |
| 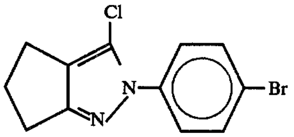 | 1/32 | 0 | 0 | 0 | 0 | 0 | 0 | 0 | 0 | | | |
| | 1/16 | 0 | 0 | 0 | 0 | 0 | 0 | 0 | 0 | | | |
| | 1/8 | 0 | 0 | 0 | 0 | 0 | 2G | 3G | 3G | | | |
| | 1/4 | 0 | 0 | 2G | 0 | 1G | 3G | 4G | 4G | | | |
| 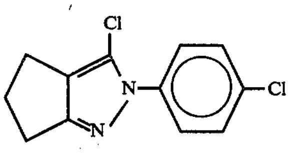 | 1/32 | 0 | 0 | 0 | 0 | — | — | — | — | | | |
| | 1/16 | 0 | 0 | 5C | 10C | — | — | — | — | | | |
| | 1/4 | — | — | 9C | 10C | — | — | — | — | | | |
| | 1/2 | 0 | 0 | 10C | 2G | — | — | — | — | | | |
| 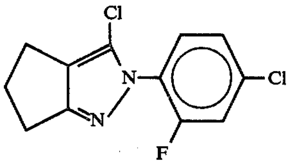 | 1/32 | 0 | 0 | 6C | 0 | — | — | — | — | | | |
| | 1/16 | 0 | 0 | 9C | 0 | — | — | — | — | | | |
| | 1/4 | 0 | — | 10C | 0 | — | — | — | — | | | |
| | 1/2 | — | — | 10C | 3G | — | — | — | — | | | |
| 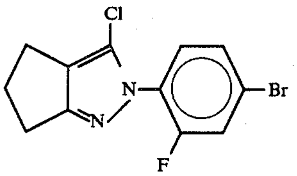 | 1/32 | 0 | 0 | 0 | 0 | 0 | 0 | 0 | 0 | | | |
| | 1/16 | 0 | — | 6G | 0 | 0 | 0 | 0 | 0 | | | |
| | 1/8 | 0 | 0 | 9C | 0 | 0 | 3G | 4G | 6G | | | |
| | 1/4 | 0 | 0 | 9C | 0 | 0 | 4G | 10C | 8C | | | |

Table 2-continued
| Compound | kg ai/ha | Postemergence | | | | | | | | | | |
|---|---|---|---|---|---|---|---|---|---|---|---|---|
| | | Inter-mediate Rice | Japonica Rice | Barn-yard-grass | Morn-ing-glory | Wheat | Wild Oats | Bromus tec-torum | Bromus secal-inus | Wild Mus-tard | Kochia | Black-grass |
| 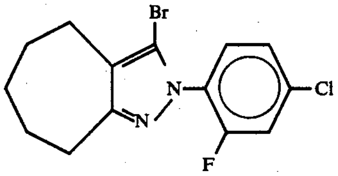 | 1/16 | | | | | | | | | | | |
| | 1/8 | | | | | | | | | | | |
| | 1/4 | | | | | | | | | | | |
| | 1/2 | | | | | | | | | | | |
| 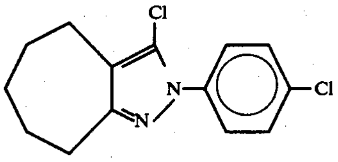 | 1/2 | 0 | 0 | 0 | 3G | | | | | | | |
| | 2 | 2G | 3G | 5B | 10B | | | | | | | |
| 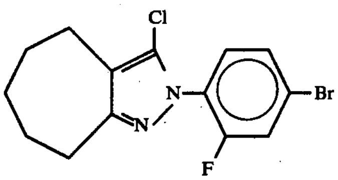 | 1/32 | | | | | | | | | | | |
| | 1/16 | | | | | | | | | | | |
| | 1/4 | | | | | | | | | | | |
| | 1/2 | | | | | | | | | | | |
| 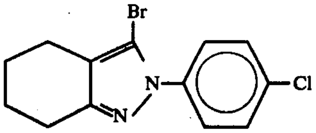 | 1/32 | | | | | | | | | | | |
| | 1/16 | | | | | | | | | | | |
| | 1/8 | | | | | | | | | | | |
| | 1/4 | | | | | | | | | | | |
| 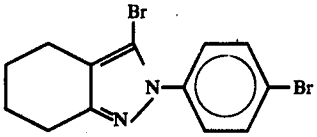 | 1/8 | | | | | | | | | | | |
| | 1/2 | | | | | | | | | | | |
| 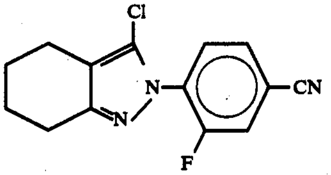 | 1/16 | | | | | | | | | | | |
| | 1/8 | | | | | | | | | | | |
| | 1/4 | | | | | | | | | | | |
| | 1/2 | | | | | | | | | | | |
| 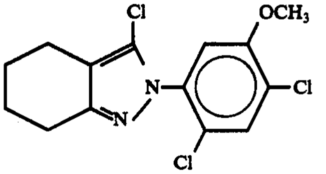 | 1/32 | | | | | | | | | | | |
| | 1/16 | | | | | | | | | | | |
| | 1/8 | | | | | | | | | | | |
| | 1/4 | | | | | | | | | | | |
| 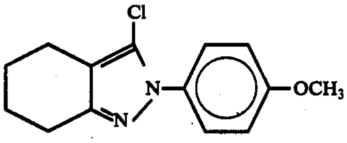 | 1/32 | 0 | 0 | 0 | — | 0 | 0 | 0 | 0 | 0 | 9B | — |
| | 1/8 | 0 | 0 | 2B | 0 | 0 | 0 | 8B | 0 | 0 | 9B | — |
| | 1/2 | 0 | 0 | 9B | 9G | 0 | 3B | 8B | 4B | 0 | 9B | — |
| 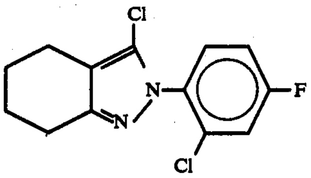 | 1/4 | | | | | | | | | | | |
| | 1 | | | | | | | | | | | |

Table 2-continued
| | |
|---|---|
| 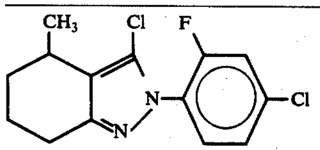 | 1/8 |
| and | |
| 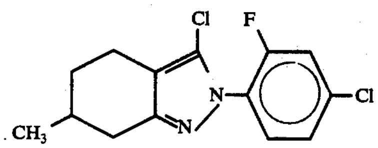 | 1/2 |
| 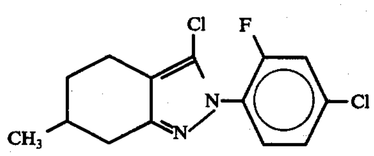 | 1/16<br>1/8<br>1/4<br>1/2 |
| 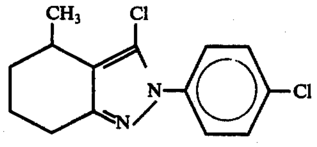 | 1/4 |
| and | |
| 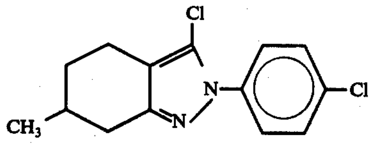 | 1 |
| 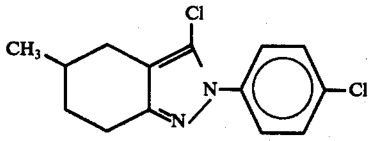 | 1/16<br>1/8<br>1/2 |
| 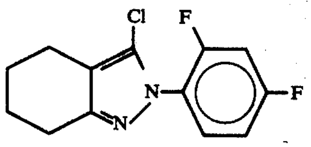 | 1/16<br>1/8<br>1/4<br>1/2 |
| 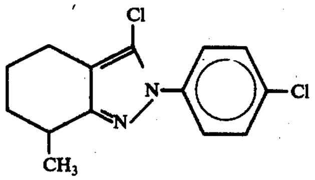 | 1/16<br>1/8<br>1/4<br>1/2 |
| 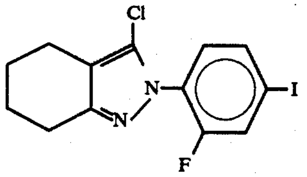 | 1/32<br>1/16<br>1/4<br>1/2 |
| 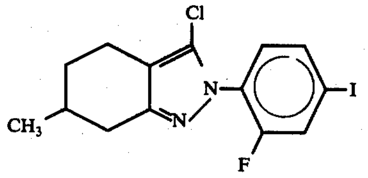 | 1/32<br>1/16<br>1/4<br>1/2 |

Table 2-continued
| | | | | | | | | | | | | |
|---|---|---|---|---|---|---|---|---|---|---|---|---|
| 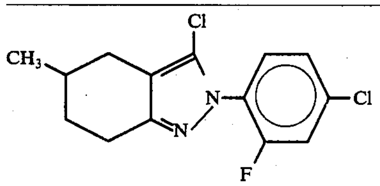 | 1/16 | | | | | | | | | | | |
| | 1/8 | | | | | | | | | | | |
| | 1/2 | | | | | | | | | | | |
| 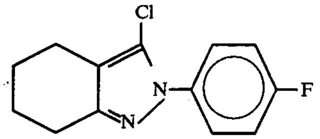 | 1/4 | 0 | 0 | 0 | 3B | 0 | 0 | 4B | 1B | | | |
| | 1/2 | 0 | 0 | 0 | 5B | 0 | 0 | 6B | 2B | | | |
| | 1 | 0 | 0 | 1B | 5B | 1B | 1B | 9B | 6B | | | |
| | 2 | 1B | 1B | 7B | 9B | 1B | 5B | 9B | 6B | | | |
| 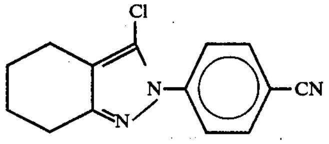 | 1/32 | | | | | | | | | | | |
| | 1/16 | | | | | | | | | | | |
| | 1/4 | | | | | | | | | | | |
| | 1/2 | | | | | | | | | | | |
| 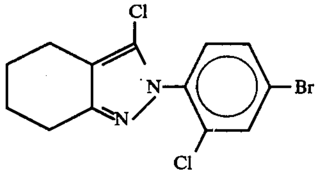 | 1/32 | | | | | | | | | | | |
| | 1/16 | | | | | | | | | | | |
| | 1/4 | | | | | | | | | | | |
| | 1/2 | | | | | | | | | | | |
| 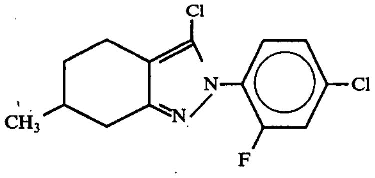 | 1/32 | 0 | 0 | 0 | — | 0 | 0 | 3B | 3B | 0 | 9B | — |
| | 1/16 | 0 | 0 | 6B | 9B | 0 | 2B | 5B | 5B | 0 | 10B | — |
| | 1/4 | 0 | 0 | 10B | 10B | 6B | 8B | 10B | 9B | 9B | 10B | — |
| | 1/2 | 2B | 4B | 10B | 10B | 5B | 10B | 9B | 10B | 10B | 9B | — |
| 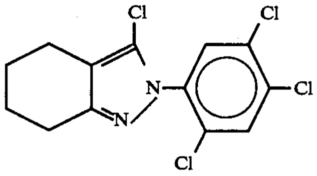 | 1/32 | | | | | | | | | | | |
| | 1/16 | | | | | | | | | | | |
| | 1/4 | | | | | | | | | | | |
| | 1/2 | | | | | | | | | | | |
| 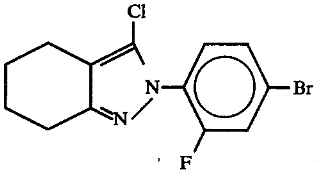 | 1/16 | | | | | | | | | | | |
| | 1/8 | | | | | | | | | | | |
| | 1/4 | | | | | | | | | | | |
| | 1/2 | | | | | | | | | | | |
| | 1 | | | | | | | | | | | |
| 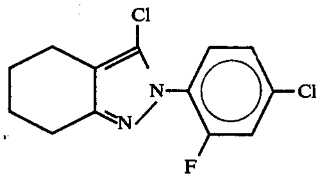 | 1/64 | 0 | 0 | 5G | 1G | 0 | 0 | 3G | 3G | 0 | — | 0 |
| | 1/32 | 0 | 0 | 6G | 7G | 0 | 6G | 7G | 7G | 0 | — | 3B |
| | 1/16 | 0 | 0 | 9B | 10B | 1G | 8G | 10B | 9B | 9B | — | 3B |
| | 1/8 | 1G | 1G | 10B | 9B | 5G | 9B | 10B | 10B | 9B | — | 9B |
| | 1/4 | 1G | 3G | 10B | 10B | 9G | 10B | 10B | 10B | 10B | — | 10B |
| 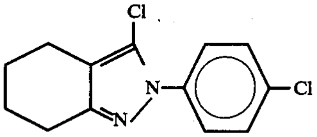 | 1/4 | 0 | 0 | 9B | 10B | 0 | 2G | 8B | 0 | 5B | 10B | 1B |
| | 1/2 | 0 | 0 | 10B | 10B | 0 | 6G | 7B | 7B | 5B | 10B | 10B |
| | 3/4 | 0 | 0 | 10B | 10B | 2G | 10B | 8B | 6B | 10B | 10B | 9B |
| | 1 | 5B | 2B | 10B | 7B | 8B | 10B | 10B | 10B | 10B | 10B | 10B |
| | 2 | 6B | 2B | 10B | — | 10B | 10B | 10B | 10B | — | — | 10B |
| 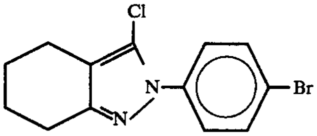 | 1/16 | | | | | | | | | | | |
| | 1/8 | | | | | | | | | | | |
| | 1/4 | | | | | | | | | | | |
| | 1/2 | | | | | | | | | | | |

Table 2-continued

| | | | | | | | | | | | | |
|---|---|---|---|---|---|---|---|---|---|---|---|---|
| 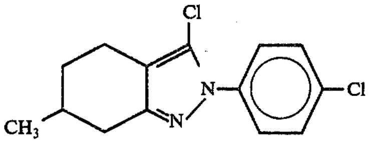 | 1/8 | 0 | 0 | 8B | — | 0 | 0 | 0 | 0 | 0 | 4B | — |
| | 1/2 | 0 | 0 | 7B | — | 0 | 0 | 0 | 0 | 2B | 8B | — |
| 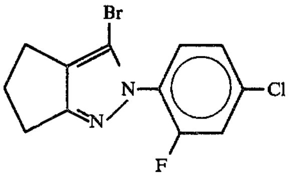 | 1/32 | | | | | | | | | | | |
| | 1/16 | | | | | | | | | | | |
| | 1/8 | | | | | | | | | | | |
| | 1/4 | | | | | | | | | | | |
| 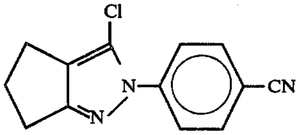 | 1/16 | | | | | | | | | | | |
| | 1/8 | | | | | | | | | | | |
| | 1/4 | | | | | | | | | | | |
| | 1/2 | | | | | | | | | | | |
| 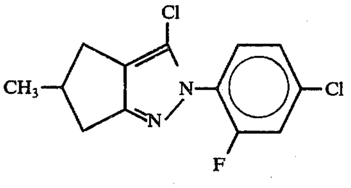 and 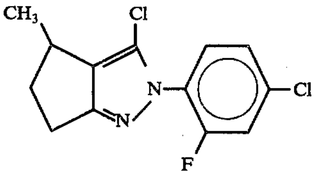 | 1/16 | | | | | | | | | | | |
| | 1/8 | | | | | | | | | | | |
| | 1/4 | | | | | | | | | | | |
| | 1/2 | | | | | | | | | | | |
| 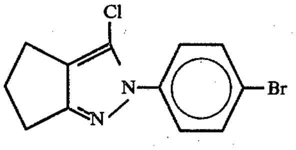 | 1/32 | | | | | | | | | | | |
| | 1/16 | | | | | | | | | | | |
| | 1/8 | | | | | | | | | | | |
| | 1/4 | | | | | | | | | | | |
| 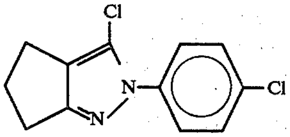 | 1/32 | | | | | | | | | | | |
| | 1/16 | | | | | | | | | | | |
| | 1/4 | | | | | | | | | | | |
| | 1/2 | | | | | | | | | | | |
| 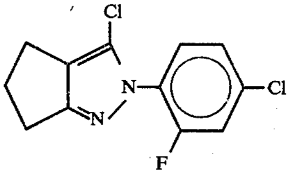 | 1/32 | | | | | | | | | | | |
| | 1/16 | | | | | | | | | | | |
| | 1/4 | | | | | | | | | | | |
| | 1/2 | | | | | | | | | | | |
| 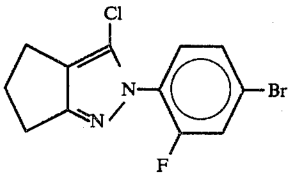 | 1/32 | | | | | | | | | | | |
| | 1/16 | | | | | | | | | | | |
| | 1/8 | | | | | | | | | | | |
| | 1/4 | | | | | | | | | | | |

It should be noted that, in general, these compounds at a low concentration virtually eliminated the undesirable vegetation, e.g., barnyardgrass, but had relatively little effect on the crops, e.g., rice. In wheat, wild oats, cheat, downy brome, and, where tested, wild mustard, Kochia, and blackgrass were controlled at a low rate with little effect on the wheat crop.

The following table, Table 3, is presented to additionally illustrate the biological activity of the compounds of the present invention. The data illustrate the herbicidal efficacy of the compounds with selectivity for rice in paddy culture.

A rice paddy was constructed using a tub containing soil and barnyardgrass (*Echinochloa crusgalli*) seeds, and japonica rice plants which were transplanted into the paddy soil when in the two to three-leaf stage. The water level was maintained a few centimeters above the soil surface. Test samples were applied directly into the paddy water, and plant response ratings were taken about three weeks later.

TABLE 3

| Structure | Rate, kg ai/ha | Japonica Rice | Barn-yard grass |
|---|---|---|---|
| 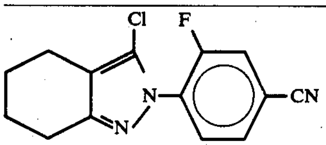 | 1/32 | 0 | 9G |
| | 1/16 | 0 | 9C |
| | 1/8 | 3B | 10C |
| 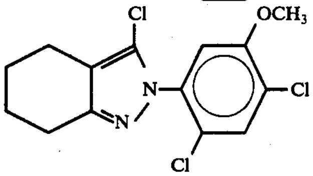 | 1/4 | 0 | 10C |
| 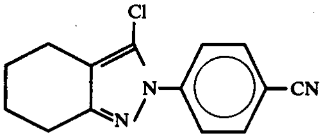 | 1/16 | 0 | 7G |
| | 1/8 | 0 | 9G |
| | 1/4 | 0 | 10C |
| | 1/2 | 2B | 9C |
| 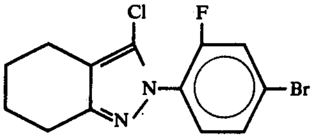 | 1/32 | 0 | 9C |
| | 1/8 | 0 | 10C |
| 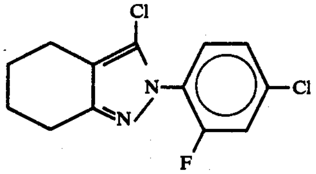 | 1/64 | 0 | 9C |
| | 1/32 | 0 | 9C |
| | 1/16 | 0 | 9C |
| | 1/8 | 1B | 10C |
| 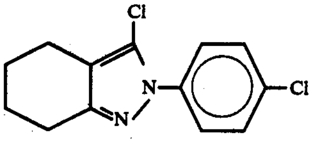 | 1/16 | 0 | 7G |
| | 1/8 | 0 | 9G |
| | 1/4 | 0 | 9C |
| | 1/2 | 1B | 10C |
| 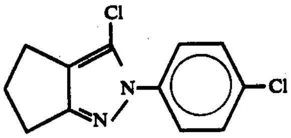 | 1/32 | 0 | 0 |
| | 1/8 | 0 | 5G |

TABLE 3-continued

| Structure | Rate, kg ai/ha | Japonica Rice | Barn-yard grass |
|---|---|---|---|
| 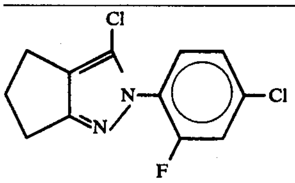 | 1/64 | 1G | 8G |

It should be noted that these compounds at a low application rate virtually eliminated the undesirable vegetation, e.g., barnyardgrass, but had relatively little effect on rice To demonstrate utility on transplanted crops, metal containers 30 × 30 33 15 cm. were filled to a depth of 13 cm. with fumigated Fallsington sandy loam soil. The following weed seeds were mixed throughout the top 2.5 cm. of soil in each container: barnyardgrass (*Echinochloa crusgalli*), crabgrass (*Digitaria sanguinalis*), giant foxtail (*Setaria faberii*), jimsonweed (*Datura stramonium*), velvetleaf (*Abutilon theophrasti*) and morningglory (*Ipomoea purpurea*).

The following treatments were applied as a pre-plant soil surface spray and also pre-plant soil incorporated (2.5 cm.)

| | | | |
|---|---|---|---|
| Control | | | |
| Compound A | 3-chloro-2-(4-chloro-2-fluorophenyl)-4,5,6,7-tetrahydro-2H-indazole | 0.016 | kg/ha |
| Compound A | | 0.12 | kg/ha |
| Compound A | | 1.0 | kg/ha |

Compound A was dislved in acetone and the solution applied at a spray volume of 560 l/ha. Immediately after treatment the following crops were transplanted: pepper (Delaware Belle, plants 12.5 cm tall), tomato (Bonny Best, plants 10 cm tall), cabbage (Wisconsin Golden Acre, plants 12.5 cm tall) and tobacco (Coker 319, plants 10 cm tall). Four plants were transplanted into each container. The containers were placed in the greenhouse and watered by hand as needed. Eighteen days after treatment the visual plant response ratings in Table 4 were recorded.

TABLE 4

| Treatment | Cabbage | Pepper | Tomato | Tobacco | Jimson-weed | Velvet-leaf | Morning-glory | Grassy Weeds |
|---|---|---|---|---|---|---|---|---|
| Pre-plant soil surface spray | | | | | | | | |
| Control | 0 | 0 | 0 | 0 | 0 | 0 | 0 | 0 |
| Compound A | | | | | | | | |
| 0.016 kg/ha | 0 | 0 | 0 | 0 | 0 | 6.8C | 0 | 4.3C |
| 0.12 | 0 | 0 | 0 | 2C | 5.5C | 10C | 0 | 9.8C |
| 1.0 | 0 | 2H,2G | 10C | 5C,3G | 10C | 10C | 2.3C,1.5G | 10C |
| Pre-plant soil inc. (2.5 cm) | | | | | | | | |
| Control | 0 | 0 | 0 | 0 | 0 | 0 | 0 | 0 |
| Compound A | | | | | | | | |
| 0.016 kg/ha | 0 | 0 | 0 | 0 | 0 | 0 | 0.3G | 1B,2G |
| 0.12 | 0 | 0 | 0 | 0 | 0 | 6.3C | 0 | 7C |
| 1.0 | 0 | 1C,2G | 1C,2H | 0 | 10C | 10C | 0 | 10C |

0 = no effect, 10 = complete control, C = chlorosis and/or necrosis, G = growth retardation and H = hormonal activity. Crop ratings are from one replication. Weed ratings are averages of four ratings (one from each crop container).

Compound A = 3-chloro-2-(4-chloro-2-fluorophenyl)-4,5,6,7-tetrahydro-2H-indazole

What is claimed is:

1. A compound of the formula

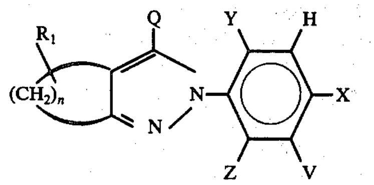

where n is 3, 4 or 5;

$R_1$ is hydrogen or methyl;

Q is fluorine, chlorine, bromime or iodine;

X is fluorine, chlorine, bromine, iodine, cyano, methoxy or nitro;

Y is hydrogen, fluorine or chlorine;

Z is hydrogen or flurorine; and

V is hydrogen, fluorine, chlorine or methoxy; with the proviso that a. when n is 5, $R_1$ must be hydrogen, Q must be chlorine or bromine, Z and V must both be hydrogen and Y must be hydrogen or fluorine;

b. when n is 3 or 4 and Q is fluorine or iodine, $R_1$, Z and Y must be hydrogen and Y must be hydrogen or fluorine;

c. when n is 3 and $R_1$ is methyl, Q must be chlorine or bromine, Y must be hydrogen or fluorine and Z and V must be hydrogen; and d. when V is other than hydrogen, X must be fluorine, chlorine or bromine and Z must be hydrogen.

2. A compound of claim 1 wherein n is 4.

3. A compound of claim 1 wherein n is 3.

4. A compound of claim 1 wherein Y is hydrogen or fluorine and Z and V are hydrogen.

5. A compound of claim 1 wherein Q is chlorine.

6. A compound of claim 1 wherein n is 4 and Q is chlorine or bromine.

7. A compound of claim 1 wherein n is 4 and Q is chlorine.

8. A compound of claim 1 wherein n is 4, Q is chlorine or bromine and $R_1$ is hydrogen.

9. A compound of claim 1 wherein n is 4, Q is chlorine and $R_1$ is hydrogen.

10. A compound of claim 1 wherein n is 4, Q is bromine and $R_1$ is hydrogen.

11. A compound of claim 1 wherein n is 3 and Q is chlorine or bromine.

12. A compound of claim 1 wherein n is 3, Q is chlorine or bromine and $R_1$ is hydrogen.

13. A compound of claim 1 wherein n is 3, Q is chlorine and $R_1$ is hydrogen.

14. A compound of claim 1 wherein Q is chlorine, Z and V are hydrogen and Y is hydrogen or fluorine.

15. A compound of claim 1 wherein n is 4, Q is chlorine, $R_1$ is hydrogen, Z is hydrogen and V is hydrogen.

16. A compound of claim 1 wherein n is 4, Q is chlorine, $R_1$ is hydrogen, Z is hydrogen, V is hydrogen, Y is hydrogen or fluorine and X is fluorine, chlorine, bromine, cyano or methoxy.

17. A compound of claim 1 wherein n is 4, Q is chlorine, $R_1$ is hydrogen, Z is hydrogen, V is hydrogen, Y is hydrogen or fluorine and X is chlorine or bromine.

18. A compound of claim 1 wherein n is 4, Q is bromine, $R_1$ is hydrogen, Z is hydrogen and V is hydrogen.

19. A compound of claim 1 wherein n is 4, Q is bromine, $R_1$ is hydrogen, Z is hydrogen, V is hydrogen, Y is hydrogen or fluorine, and X is fluorine, chlorine, bromine, cyano or methoxy.

20. A compound of claim 1 wherein n is 4, Q is bromine, $R_1$ is hydrogen, Z is hydrogen, V is hydrogen, Y is hydrogen or fluorine, and X is chlorine or bromine.

21. A compound of claim 1 wherein n is 3, Q is chlorine, $R_1$ is hydrogen, Z is hydrogen and V is hydrogen.

22. A compound of claim 1 wherein n is 3, Q is chlorine, $R_1$ is hydrogen, Z is hydrogen, V is hydrogen, Y is hydrogen or fluorine, and X is fluorine, chlorine, bromine, cyano or methoxy.

23. A compound of claim 1 wherein n is 3, Q is chlorine, $R_1$ is hydrogen, Z is hydrogen, V is hydrogen, Y is hydrogen or fluorine, and X is chlorine or bromine.

24. A compound of claim 1 wherein Q is chlorine, Z is hydrogen, V is hydrogen, Y is hydrogen or fluorine and X is chlorine or bromine.

25. A compound of claim 1 wherein n is 3, Q is bromine, Z is hydrogen, V is hydrogen, Y is hydrogen or fluorine and X is chlorine or bromine.

26. The compound of claim 1, 3-chloro-2-(4-chloro-2-fluorophenyl)-4,5,6,7-tetrahydro-2H-indazole.

27. The compound of claim 1, 3-chloro-2-(4-chlorophenyl)-4,5,6,7-tetrahydro-2H-indazole.

28. The compound of claim 1, 3-bromo-2-(4-chloro-2-fluorophenyl)-4,5,6,7-tetrahydro-2H-indazole.

29. The compound of claim 1, 3-chloro-2-(4-bromo-2-fluorophenyl)-4,5,6,7-tetrahydro-2H-indazole.

30. The compound of claim 1, 3-chloro-2-(4-chloro-2-fluorophenyl)-2,4,5,6-tetrahydrocyclopentapyrazole.

31. The compound of claim 1, 3-chloro-2-(4-chlorophenyl)-2,4,5,6-tetrahydrocyclopentapyrazole.

32. A composition for the control of undesirable vegetation consisting essentially of an effective amount of a compound of claim 1 and at least one of (a) an inert surface-active agent, and (b) a solid or liquid diluent.

33. A composition for the control of undesirable vegetation consisting essentially of an effective amount of a compound of claim 2 and at least one of (a) an inert surface-active agent, and (b) a solid or liquid diluent.

34. A composition for the control of undesirable vegetation consisting essentially of an effective amount of a compound of claim 3 and at least one of (a) an inert surface-active agent, and (b) a solid or liquid diluent.

35. A composition for the control of undesirable vegetation consisting essentially of an effective amount of a compound of claim 4 and at least one of (a) an inert surface-active agent, and (b) a solid or liquid diluent.

36. A composition for the control of undesirable vegetation consisting essentially of an effective amount of a compound of claim 5 and at least one of (a) an inert surface-active agent, and (b) a solid or liquid diluent.

37. A composition for the control of undesirable vegetation consisting essentially of an effective amount of a compound of claim 6 and at least one of (a) an inert surface-active agent, and (b) a solid or liquid diluent.

38. A composition for the control of undesirable vegetation consisting essentially of an effective amount of a compound of claim 7 and at least one of (a) an inert surface-active agent, and (b) a solid or liquid diluent.

39. A composition for the control of undesirable vegetation consisting essentially of an effective amount of a compound of claim 8 and at least one of (a) an inert surface-active agent, and (b) a solid or liquid diluent.

40. A composition for the control of undesirable vegetation consisting essentially of an effective amount of a compound of claim 9 and at least one of (a) an inert surface active agent and (b) a solid or liquid diluent.

41. A composition for the control of undesirable vegetation consisting essentially of an effective amount of a compound of claim 10 and at least one of (a) an inert surface-active agent, and (b) a solid or liquid diluent.

42. A composition for the control of undesirable vegetation consisting essentially of an effective amount of claim 11 and at least one of (a) an inert surface-active agent, and (b) a solid or liquid diluent.

43. A composition for the control of undesirable vegetation consisting essentially of an effective amount of a compound of claim 12 and at least one of (a) an inert surface-active agent, and (b) a solid or liquid diluent.

44. A composition for the control of undesirable vegetation consisting essentially of an effective amount of a compound of claim 13 and at least one of (a) an inert surface-active agent, and (b) a solid or liquid diluent.

45. A composition for the control of undesirable vegetation consisting essentially of an effective amount of a compound of claim 14 and at least one of (a) an inert surface-active agent, and (b) a solid or liquid diluent.

46. A composition for the control of undesirable vegetation consisting essentially of an effective amount of a compound of claim 15 and at least one of (a) an inert surface-active agent, and (b) a solid or liquid diluent.

47. A composition for the control of undesirable vegetation consisting essentially of an effective amount of a compound of claim 16 and at least one of (a) an inert surfact-active agent, and (b) a solid or liquid diluent.

48. A composition for the control of undesirable vegetation consisting essentially of an effective amount of a compound of claim 17 and at least one of (a) an inert surface-active agent, and (b) a solid or liquid diluent.

49. A composition for the control of undesirable vegetation consisting essentially of an effective amount of a compound of claim 18 and at least one of (a) an inert surface-active agent, and (b) a solid or liquid diluent.

50. A composition for the control of undesirable vegetation consisting essentially of an effective amount of a compound of claim 19 and at least one of (a) an inert surface-active agent, and (b) a solid or liquid diluent.

51. A composition for the control of undesirable vegetation consisting essentially of an effective amount of a compound of claim 20 and at least one of (a) an inert surface-active agent, and (b) a solid or liquid diluent.

52. A composition for the control of undesirable vegetation consisting essentially of an effective amount of claim 21 and at least one of (a) an inert surface-active agent, and (b) a solid or liquid diluent.

53. A compositon for the control of undesirable vegetation consisting essentially of an effective amount of a compound of claim 22 and at least one of (a) an inert surface-active agent, and (b) a solid or liquid diluent.

54. A composition for the control of undesirable vegetation consisting essentially of an effective amount of a compound of claim 23 and at least one of (a) an inert surface-active agent, and (b) a solid or liquid diluent.

55. A composition for the control of undesirable vegetation consisting essentially of an effective amount of a compound of claim 24 and at least one of (a) an inert surface-active agent, and (b) a solid or liquid diluent.

56. A composition for the control of undesirable vegetation consisting essentially of an effective amount of a compound of claim 25 and at least one of (a) an inert surface-active agent, and (b) a solid or liquid diluent.

57. A compositon for the control of undesirable vegetation consisting essentially of an effective amount of the compound of claim 26 and at least one of (a) an inert surface-active agent, and (b) a solid or liquid diluent.

58. A composition for the control of undesirable vegetation consisting essentially of an effective amount of the compound of claim 27 and at least one of (a) an inert surface-active agent, and (b) a solid or liquid diluent.

59. A composition for the control of undesirable vegetation consisting essentially of an effective amount of the compound of claim 28 and at least one of (a) an inert surface-active agent, and (b) a solid or liquid diluent.

60. A composition for the control of undesirable vegetation consisting essentially of an effective amount of the compound of claim 29 and at least one of (a) an inert surface-active agent, and (b) a solid or liquid diluent.

61. A composition for the control of undesirable vegetation consisting essentially of the compound of an effective amount of claim 30 and at least one of (a) an inert surface-active agent, and (b) a solid or liquid diluent.

62. A composition for the control of undesirable vegetation consisting essentially of an effective amount of the compound of claim 31 and at least one of (a) an inert surface-active agent, and (b) a solid or liquid diluent.

63. A method for the control of undesirable vegetation comprising applying to the locus of such undesirable vegetation a herbicidally effective amount of a compound of claim 1.

64. A method for the control of undesirable vegetation comprising applying to the locus of such undesirable vegetation a herbicidally effective amount of a compound of claim 2.

65. A method for the control of undesirable vegetation comprising applying to the locus of such undesirable vegetation a herbicidally effective amount of a compound of claim 3.

66. A method for the control of undesirable vegetation comprising applying to the locus of such undesirable vegetation a herbicidally effective amount of a compound of claim 4.

67. A method for the control of undesirable vegetation comprising applying to the locus of such undesirable vegetation a herbicidally effective amount of a compound of claim 5.

68. A method for the control of undesirable vegetation comprising applying to the locus of such undesirable vegetation a herbicidally effective amount of a compound of claim 6.

69. A method for the control of undesirable vegetation comprising applying to the locus of such undesirable vegetation a herbicidally effective amount of a compound of claim 7.

70. A method for the control of undesirable vegetation comprising applying to the locus of such undesirable vegetation a herbicidally effective amount of a compound of claim 8.

71. A method for the control of undesirable vegetation comprising applying to the locus of such undesirable vegetation a herbicidally effective amount of a compound of claim 9.

72. A method for the control of undesirable vegetation comprising applying to the locus of such undesirable vegetation a herbicidally effective amount of a compound of claim 10.

73. A method for the control of undesirable vegetation comprising applying to the locus of such undesirable vegetation a herbicidally effective amount of a compound of claim 11.

74. A method for the control of undesirable vegetation comprising applying to the locus of such undesirable vegetation a herbicidally effective amount of a compound of claim 12.

75. A method for the control of undesirable vegetation comprising applying to the locus of such undesirable vegetation a herbicidally effective amount of a compound of claim 13.

76. A method for the control of undesirable vegetation comprising applying to the locus of such undesirable vegetation a herbicidally effective amount of a compound of claim 14.

77. A method for the control of undesirable vegetation comprising applying to the locus of such undesirable vegetation a herbicidally effective amount of a compound of claim 15.

78. A method for the control of undesirable vegetation comprising applying to the locus of such undesirable vegetation a herbicidally effective amount of a compound of claim 16.

79. A method for the control of undesirable vegetation comprising applying to the locus of such undesirable vegetation a herbidically effective amount of a compound of claim 17.

80. A method for the control of undesirable vegetation comprising applying to the locus of such undesirable vegetation a herbidically effective amount of a compound of claim 18.

81. A method for the control of undesirable vegetation comprising applying to the locus of such undesirable vegetation a herbicidally effective amount of a compound of claim 19.

82. A method for the control of undesirable vegetation comprising applying to the locus of such undesirable vegetation a herbicidally effective amount of a compound of claim 20.

83. A method for the control of undesirable vegetation comprising applying to the locus of such undesirable vegetation a herbicidally effective amount of a compound of claim 21.

84. A method for the control of undesirable vegetation comprising applying to the locus of such undesirable vegetation a herbicidally effective amount of a compound of claim 22.

85. A method for the control of undesirable vegetation comprising applying to the locus of such undesirable vegetation a herbicidally effective amount of a compound of claim 23.

86. A method for the control of undesirable vegetation comprising applying to the locus of such undesirable vegetation a herbicidally effective amount of a compound of claim 24.

87. A method for the control of undesirable vegetation comprising applying to the locus of such undesirable vegetation a herbicidally effective amount of a compound of claim 25.

88. A method for the control of undesirable vegetation comprising applying to the locus of such undesirable vegetation a herbicidally effective amount of the compound of claim 26.

89. A method for the control of undesirable vegetation comprising applying to the locus of such undesirable vegetation a herbicidally effective amount of the compound of claim 27.

90. A method for the control of undesirable vegetation comprising applying to the locus of such undesirable vegetation a herbicidally effective amount of the compound of claim 28.

91. A method for the control of undesirable vegetation comprising applying to the locus of such undesirable vegetation a herbicidally effective amount of the compound of claim 29.

92. A method for the control of undesirable vegetation comprising applying to the locus of such undesirable vegetation a herbicidally effective amount of the compound of claim 30.

93. A method for the control of undesirable vegetation comprising applying to the locus of such undesirable vegetation a herbicidally effective amount of the compound of claim 31.

94. A method for the control of undesirable vegetation in rice consisting essentially of applying to the locus of such undesirable vegetation a herbicidally effective amount of a compound of claim 1.

95. The method of claim 94, wherein said undesirable vegetation is barnyard grass.

96. The method of claim 94, wherein the compound is 3-chloro-2-(4-chloro-2-fluorophenyl)-4,5,6,7-tetrahydro-2H-indazole.

97. The method of claim 94, wherein the compound is 3-chloro-2-(4-chlorophenyl)-4,5,6,7-tetrahydro-2H-indazole.

98. The method of claim 96, wherein the rice is paddyrice.

99. The method of claim 97, wherein the rice is paddyrice.

100. A method for the control of undesirable vegetation in wheat which comprises applying to the locus of such undesirable vegetation a herbicidally effective amount of the compound of claim 1.

101. The method of claim 100, wherein the compound is 3-chloro-2-(4-chloro-2-fluorophenyl)-4,5,6,7-tetrahydro-2H-indazole.

102. The method of claim 100, wherein the compound is 3-chloro-2-(4-chlorophenyl)-4,5,6,7-tetrahydro-2H-indazole.

103. A method for the control of undesirable vegetation in transplanted crops consisting essentially of applying to the locus of such undesirable vegetation a herbicidally effective amount of the compound of claim 1.

104. The method of claim 103, wherein the compound is 3-chloro-2-(4-chloro-2-fluorophenyl)-4,5,6,7-tetrahydro-2H-indazole.

105. The method of claim 103, wherein the compound is 3-chloro-2-(4-chlorophenyl)-4,5,6,7-tetrahydro-2H-indazole.

* * * * *